United States Patent
Van Der Maas

(10) Patent No.: US 11,317,574 B2
(45) Date of Patent: May 3, 2022

(54) **ANGULAR LEAF SPOT (*PSEUDOMONAS*) RESISTANCE IN CUCUMBER**

(71) Applicant: RIJK ZWAAN ZAADTEELT EN ZAADHANDEL B.V., De Lier (NL)

(72) Inventor: Cornelis Van Der Maas, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 16/594,755

(22) Filed: Oct. 7, 2019

(65) Prior Publication Data
US 2020/0056201 A1    Feb. 20, 2020

Related U.S. Application Data

(63) Continuation-in-part of application No. PCT/EP2018/059039, filed on Apr. 9, 2018.

(30) Foreign Application Priority Data

Apr. 7, 2017    (WO) .................. PCT/EP2017/058434

(51) Int. Cl.
| | | |
|---|---|---|
| *A01H 1/04* | (2006.01) | |
| *A01H 5/08* | (2018.01) | |
| *C12N 9/02* | (2006.01) | |
| *C12Q 1/6895* | (2018.01) | |
| *A01H 6/34* | (2018.01) | |

(52) U.S. Cl.
CPC .............. *A01H 1/04* (2013.01); *A01H 5/08* (2013.01); *A01H 6/346* (2018.05); *C12N 9/0071* (2013.01); *C12Q 1/6895* (2013.01); *C12Y 114/11012* (2013.01); *C12Q 2600/13* (2013.01); *C12Q 2600/156* (2013.01)

(58) Field of Classification Search
CPC combination set(s) only.
See application file for complete search history.

(56) References Cited

U.S. PATENT DOCUMENTS

2009/0210964 A1    8/2009    Shetty et al.

FOREIGN PATENT DOCUMENTS

WO    2014/085763 A1    6/2014

OTHER PUBLICATIONS

H. Olczak-Woltman, et al., Inheritance of Resistance to Angular Leaf Spot (*Pseudomonas syringae* pv. *Lachrymans*) in Cucumber and Identification of Molecular Markers Linked to Resistance, Plant Pathology (2009) vol. 58, p. 145-151.
H. Olczak-Woltman, et al., Evaluation of Cucumber (*Cucumis sativus*) Cultivars Grown in Eastern Europe and Progress in Breeding for Resistance to Angular Leaf Spot (*Pseudomonas syringae* pv. *Lachrymans*) Eur. J. Plant Pathol (2003) vol. 122, p. 385-393.
Database Accession No. CCD28480: Jun. 13, 2013—*Cucumis sativus* (Cucumber) retrieved from: http:/www.ebi.ac.uk/ena/data/view/CCD28480&display=text).
International Search Report and Written Opinion dated Aug. 29, 2018 in PCT/EP2018/059039.

*Primary Examiner* — Brent T Page
(74) *Attorney, Agent, or Firm* — Duane Morris LLP; Thomas J. Kowalski; Deborah. L. Lu

(57) ABSTRACT

The present invention relates to a cucumber plant (*Cucumis sativus* L.) that is resistant to *Pseudomonas syringae* pv. *lachrymans*, a pathogen that causes angular leaf spot disease in cucumber. The invention further relates to markers linked to the resistance and the use of markers to identify resistant plants. The invention also relates to seed and progeny of such plants and to propagation material derived from such plants and for obtaining such plants. Furthermore, the invention relates to methods for producing, identifying and selecting *Pseudomonas* resistant cucumber plants, and for producing hybrid plant seed. The invention further relates to the use of a gene and/or QTLs and sequences thereof to identify/select *Pseudomonas* resistant cucumber plants.

18 Claims, No Drawings

Specification includes a Sequence Listing.

ANGULAR LEAF SPOT (*PSEUDOMONAS*) RESISTANCE IN CUCUMBER

RELATED APPLICATIONS AND INCORPORATION BY REFERENCE

This application is a continuation-in-part application of international patent application Serial No. PCT/EP2018/059039 filed 9 Apr. 2018, which published as PCT Publication No. WO 2018/185340 on 11 Oct. 2018, which claims benefit of international patent application Serial No. PCT/EP2017/058434 filed 7 Apr. 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named 00436SL.txt and is 20.2 kbytes in size.

FIELD OF THE INVENTION

The present invention relates to a cucumber plant (*Cucumis sativus* L.) that is resistant to *Pseudomonas syringae* pv. *lachrymans*, the pathogen that causes angular leaf spot disease in cucumber. The invention further relates to markers linked to the resistance and the use of markers to identify and/or develop resistant plants. The invention also relates to seed and progeny of such plants and to propagation material derived from such plants and for obtaining such plants. Furthermore, the invention relates to methods for producing, identifying and selecting *Pseudomonas* resistant cucumber plants, and for producing hybrid cucumber seed.

BACKGROUND OF THE INVENTION

Cucumber plants (or also named cucumbers) of the species *Cucumis sativus* belong to the cucurbit family, scientifically named the Cucurbitaceae. The species is part of the genus *Cucumis*, which contains the important food crop cucumber, *Cucumis sativus*, and also a variety of melon types mostly included in the species *Cucumis melo*, as well as several other, less well-known species. Cucumber is an annual, herbaceous, flowering plant species which is thought to have originated in Asia.

Cucumber plants were domesticated early and have been cultivated for thousands of years in African and Asian countries. Cucumber is a diploid plant species with seven pairs of chromosomes. Cultivated cucumber plants have male and female flowers, which can be present together in monoecious plants, but in present-day cultivars commonly gynoecious (all female) plants are used. Cucumbers are easy cross-pollinators but can also self-pollinate when female and male flowers are present in the same plant. Cucumbers are presently cultivated worldwide in a large variety of types, which typically differ in size, color, and skin type. Cucumber production is most successful in a relatively warm climate and it prefers temperatures between about 18-25° C. Several pests and diseases can affect cucumber production, including several viruses that are often transferred by insects, but also bacterial and fungal diseases. One of these major pests that can threaten cucumber harvest is angular leaf spot.

Angular leaf spot is a severe disease in Cucurbits and is caused by the bacterium *Pseudomonas syringae* pv. *lachrymans*. The bacterial disease can occur on most cucurbits, including cucumber, muskmelon, pumpkin, and winter squash. The disease has a worldwide distribution and has been observed to emerge under humid and wet conditions. *Pseudomonas syringae* pv. *lachrymans* is most active between 24° and 28° C. and is favored by high relative humidity (higher than 95%). As the name of the disease indicates, the leaf spots that are caused by the disease are angular because the surrounding leaf veins limit the enlargement of the spots. The initial symptoms are brown water soaked spots, which may be surrounded by a yellow halo. Older spots become white, dry out and tear from the surrounding healthy tissue, leaving irregular holes behind in the affected leaves. In moist conditions, a white milky exudate made of bacteria forms on the lesions and dries to a thin white crust. Heavily infected leaves may turn yellow overall. Lesions with or without halos may also appear on petioles and stems. On fruit, smaller circular spots may appear that often crack open and turn white, allowing also other pathogens to contaminate fruit and cause fruit rot. Splashing rain spreads bacteria from the soil to plant parts and from plant to plant. The bacteria can also be easily spread in the field through people, insects, cultivation equipment, and harvesters. The bacteria can survive in contaminated seed, soil or debris from diseased plants.

Citation or identification of any document in this application is not an admission that such document is available as prior art to the present invention.

SUMMARY OF THE INVENTION

In cucumber cultivation there is a need for resistance to *Pseudomonas syringae* pv. *lachrymans*. It is therefore an object of the present invention to provide a cucumber plant with a resistance to *Pseudomonas syringae* pv. *lachrymans*.

It is further an object of the present invention to provide molecular markers to identify and/or assist in the development of cucumber plants carrying one or more genes or QTLs causing resistance *Pseudomonas syringae* pv. *lachrymans*. The terms "*Pseudomonas*", "angular leaf spot" and "*Pseudomonas syringae* pv. *lachrymans*" as used in this patent application are used interchangeably.

In the research that led to the current invention, angular leaf spot (*Pseudomonas syringae* pv. *lachrymans*) resistance in cucumber plants was identified and characterized. Cucumber plants with angular leaf spot (*Pseudomonas syringae* pv. *lachrymans*) resistance can be used in the development of commercial high-end cucumber varieties. Cucumber plants were developed that are resistant against *Pseudomonas syringae* pv. *lachrymans*.

In the research leading to the invention, the resistance to *Pseudomonas syringae* pv. *lachrymans* as present in cucumber plants belonging to an internal breeding line was characterized. A QTL mapping study was done using these resistant plants to identify the genetic regions that cause the resistance against *Pseudomonas syringae* pv. *lachrymans*. In this study it was found that the resistance to *Pseudomonas syringae* pv. *lachrymans* is controlled by a gene and optionally several minor QTLs (quantitative trait loci) located on different chromosomes. A plant that has a mutant allele of the gene and optionally one or more minor mutant alleles of the QTLs shows resistance to *Pseudomonas syringae* pv. *lachrymans*. The mutant allele of the gene and the mutant alleles of the QTLs involved in the absence/presence of *Pseudomonas syringae* pv. *lachrymans* resistance were further characterised. The gene involved in the presence of resistance to *Pseudomonas syringae* pv. *lachrymans* is the Gibberellin-20-oxidase gene.

Accordingly, it is an object of the invention not to encompass within the invention any previously known product, process of making the product, or method of using the product such that Applicants reserve the right and hereby disclaim of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of cucumber *Cucumis sativus* EX5010 that comprise the mutant allele of the Gibberellin-20-oxidase gene and the mutant alleles of QTL2, QTL3, QTL4, and QTL5 homozygously and have the phenotypic trait of the invention, were deposited with NCIMB Ltd, Ferguson Building, Craibstone Estate, Bucksburn, Aberdeen AB21 9YA, UK on 3 Jun. 2016 under deposit accession number NCIMB 42582.

The Deposits with NCIMB Ltd, under deposit accession number 42582 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention relates to a cucumber plant that may comprise a mutant allele of the Gibberellin-20-oxidase gene, that confers resistance to *Pseudomonas syringae* pv. *lachrymans* to the plant. The mutant allele of the cucumber Gibberellin-20-oxidase gene is as found in a cucumber plant, representative seed of which was deposited under deposit number NCIMB 42582.

The mutant allele of the Gibberellin-20-oxidase gene referred to herein is a dominant allele of the Gibberellin-20-oxidase gene, conferring resistance to *Pseudomonas*. The plant of the invention, which is resistant to *Pseudomonas syringae* pv. *lachrymans*, may therefore comprise the mutant allele of the Gibberellin-20-oxidase gene either homozygously or heterozygously.

The plant of the invention may comprise a mutant allele of the Gibberellin-20-oxidase gene that has a Single Nucleotide Polymorphism (SNP) on a position that leads to a change in the wild type amino acid sequence of the Gibberellin-20-oxidase protein. A Single Nucleotide Polymorphism (SNP) is a single nucleotide variation in a DNA sequence among individual plants. SNPs may occur within coding sequences of genes, non-coding regions of genes, or in the intergenic regions. SNPs in the coding region can be synonymous and non-synonymous. The so-called synonymous SNPs do not affect the protein sequence, while non-synonymous SNPs change the amino acid sequence of protein.

In an embodiment of the invention, the SNP in the Gibberelline-20-oxidase gene is found on position 860 of the wild type nucleotide sequence of SEQ ID NO:1, leading to a change in the wild type amino acid sequence of the Gibberellin-20-oxidase protein.

In an embodiment of the invention, the change in the wild type amino acid sequence of the Gibberellin-20-oxidase protein is an amino acid substitution on position 287 of the wild type amino acid sequence of SEQ ID NO:3. In an embodiment of the invention, the SNP may comprise a change from guanine to adenine. In an embodiment of the invention, the mutant allele of the Gibberellin-20-oxidase gene may comprise SEQ ID NO:2.

The wild type nucleotide sequence SEQ ID NO:1, the mutant nucleotide sequence SEQ ID NO:2, the wild type amino acid sequence SEQ ID NO:3 and the mutant amino acid sequence SEQ ID NO:4 can be found in Table 1.

Wild type refers generally to the phenotype and/or genotype of the typical form of a species, genotype or gene as it occurs most commonly in nature, in contrast to a mutant or modified form. In this context it refers to the nucleotide sequence of the Gibberelline-20-oxidase gene, and the encoded amino acid sequence of the Gibberelline-20-oxidase protein that when present in a cucumber plant do not result in resistance to *Pseudomonas syringae* pv. *lachrymans*.

The SNP in the Gibberellin-20-oxidase gene sequence leads to an amino acid substitution from cysteine (C) to tyrosine (Y), in the Gibberelline-20-oxidase protein.

The amino acid substitution caused by the nucleotide mutation of the current invention was found on position 287 of the cucumber amino acid sequence of SEQ ID NO:3 resulting in amino acid sequence SEQ ID NO:4. The amino acid sequence SEQ ID NO:3 and SEQ ID NO:4 can be found in Table 1.

The nucleotide mutation is considered to be non-conservative, and the amino acid change can be considered non-conservative. Amino acid changes in a protein occur when the mutation of one or more base pairs in the coding DNA sequence result in an altered codon triplet that encodes a different amino acid. Not all (point) mutations in coding DNA sequence lead to amino acid changes. Mutations in the coding sequence that do not lead to amino acid changes are called "silent mutations". Other mutations are called "conservative"; they lead to the replacement of one amino acid by another amino acid with comparable properties, such that the mutations are unlikely to change the folding of the mature protein, or influence its function. Non-conservative mutations in a coding DNA sequence lead to change(s) in the amino acid sequence, as in the current invention.

As used herein a "non-conservative amino acid change" refers to an amino acid that is replaced by another amino acid that has different chemical properties that may lead to decreased stability, changed functionality and/or structural effects of the encoded protein.

The plant of the invention may have the mutant allele of the Gibberellin-20-oxidase gene in homozygous or heterozygous state. Both homozygous and heterozygous plants can be used as a potential source of the mutant allele of the Gibberellin-20-oxidase gene. When a plant having the mutant allele of the Gibberellin-20-oxidase gene heterozygously is crossed with another plant that does not show the resistance, at least part of the progeny of the cross shows the trait of resistance to Pseudomonas syringae pv. lachrymans. When a non-resistant plant is crossed with a plant that is homozygous for the mutant allele of the Gibberellin-20-oxidase gene the complete progeny will be resistant.

It was furthermore found according to the invention, that in addition to the mutant allele of the Gibberelline-20-oxidase gene located on chromosome 6, mutant alleles of four minor QTLs contribute to cucumber plant resistance against Pseudomonas syringae pv. lachrymans.

A QTL, located on chromosome 2, was designated QTL2. In the seeds of deposit NCIMB 42582, QTL2 is located between flanking markers M5007 and M5609. The marker M5007 is represented by sequences SEQ ID NO:5 and SEQ ID NO:6 and marker M5609 by SEQ ID NO:9 and SEQ ID NO:10. In the seeds of the deposit, the resistance conferring allele of QTL2 is linked to sequence SEQ ID NO:8 of marker M5009. The susceptible allele of QTL2 is linked to the SNP as present in the sequence SEQ ID NO:7. QTL2 is located within 20 cM or 10 cM or 5 cM of the markers.

A QTL, located on chromosome 5, was designated QTL3. In the seeds of deposit NCIMB 42582, QTL3 is located between flanking markers M1000 and M3418. The marker M1000 is represented by SEQ ID NO:11 and SEQ ID NO:12 and marker M3418 is represented by sequences SEQ ID NO:15 and SEQ ID NO:16. In the seeds of the deposit, the resistance conferring allele of QTL3 is linked to the SNP as present in the sequence SEQ ID NO:14 of marker M2071. The susceptible allele of QTL3 is linked to the SNP as present in the sequence SEQ ID NO:13. QTL3 is located within 20 cM or 10 cM or 5 cM of the markers.

A QTL, located on chromosome 7, was designated QTL4. In the seeds of deposit NCIMB 42582, QTL4 is located between flanking markers M1520 and M0459. The marker M1520 is represented by sequences SEQ ID NO:23 and SEQ ID NO:24 and marker M0459 is represented by sequences SEQ ID NO:27 and SEQ ID NO:28. In the seeds of the deposit, the resistance conferring allele of QTL4 is linked to the SNP as present in the sequence SEQ ID NO:26 of marker M5644. The susceptible allele of QTL4 is linked to the SNP as present in the sequence SEQ ID NO:25. QTL4 is located within 20 cM or 10 cM or 5 cM of the markers.

A QTL, located on chromosome 7, was designated QTL5. In the seeds of deposit NCIMB 42582, QTL5 is located between flanking markers M5843 and M0205. The marker M5843 is represented by sequences SEQ ID NO:29 and SEQ ID NO:30 and marker M0205 is represented by sequences SEQ ID NO:33 and SEQ ID NO:34. In the seeds of the deposit, the resistance conferring allele of QTL5 is linked to the SNP as present in the sequence SEQ ID NO:32 of marker M5618. The susceptible allele of QTL5 is linked to the SNP as present in the SEQ ID NO:31. QTL5 is located within 20 cM or 10 cM or 5 cM of the markers.

The QTL that is located on chromosome 7, designated as QTL5, is possibly similar to the Ethylene-responsive transcription factor-like protein gene, abbreviated name ERLF1_ARATH (At4g13040).

The resistance conferring alleles of the QTLs as defined herein are also referred to as mutant alleles of the QTLs of the invention. The cucumber plant of the invention preferably may comprise a combination of the mutant allele of the Gibberellin-20-oxidase gene and one or more of the Pseudomonas syringae pv. lachrymans mutant alleles of a QTL of the invention.

A QTL (Quantitative Trait Locus) may comprise the genetic information in the genome of the plant that causes a trait of interest. A QTL may comprise a gene or can be closely linked to a gene that controls the trait. The variation in the locus of the QTL is correlated with the variation found in the phenotype, in this particular case the Pseudomonas syringae pv. lachrymans resistance. When a plant shows the trait of the invention, its genome may comprise the mutant allele of the Gibberellin-20-oxidase gene and optionally one or more mutant alleles of the QTLs contributing to the trait of the invention.

Flanking markers mark the borders of a region where a gene or a QTL of interest is situated. They are not necessarily linked to the trait caused by the gene/QTL. However, a skilled person can use the sequence information of the flanking markers to position these markers on a genetic map and thereby also determine the region/locus of interest where the QTL/gene is situated on a genetic map. Linked markers are linked to the gene or QTL of interest. This means that the DNA sequence of a linked marker is positioned close enough to the causal gene of the trait to be inherited together. If a plant may comprise the DNA sequence of a linked marker of the invention, it is resistant to Pseudomonas syringae pv. lachrymans.

The term "allele" as used herein is a variant form of a gene or QTL. Mutations (including SNPs) in the DNA sequence of genes or QTLs can lead to different forms, known as alleles. Alleles may encode slightly different versions of a protein, which then can cause different phenotypic traits.

The word "trait" in the context of this application refers to the phenotype of the plant. In particular, the word "trait" refers to the trait of the invention, more in particular to the trait of resistance to Pseudomonas syringae pv. lachrymans.

The term "resistance to Pseudomonas syringae pv. lachrymans" as used herein, refers to the phenotypic trait of resistance to Pseudomonas syringae pv. lachrymans. To determine the presence of Pseudomonas syringae pv. lachrymans resistance, a bioassay can be performed. Bioassays can be performed in several ways, as known by a person skilled in the art. Example 1 describes a suitable bioassay for determining if a plant shows *Pseudomonas syringae* pv. *lachrymans* resistance. In this test, a plant with a *Pseudomonas syringae* pv. *lachrymans* resistance score of, on average in order of increased preference, at least 1.0 lower, at least 1.5 lower, at least 2.0 lower, at least 2.5 lower, at least 3.5 lower, at least 4.0 lower, at least 4.5 lower, on a scale of 1.0 to 5.0, than the *Pseudomonas syringae* pv. *lachrymans* resistance score of an isogenic cucumber plant not having the mutant allele of the Gibberellin-20-oxidase gene and optionally one or more of the mutant alleles of a QTL of the invention, is considered to show resistance to *Pseudomonas syringae* pv. *lachrymans* and is thus considered a plant of the invention. An isogenic cucumber plant is a cucumber plant that is genotypically the same but does not have the mutant allele of the Gibberellin-20-oxidase gene and optionally one or more of the mutant alleles of a QTL of the invention.

In the above test, the average disease score of a cucumber plant not having the mutant allele of the Gibberelline-20-oxidase gene or any of the mutant alleles of the QTLs of the invention, was 5.0, set against a scale of 1.0 to 5.0. A cucumber plant which may comprise the mutant allele of the Gibberellin-20 oxidase gene of the invention showed an average *Pseudomonas syringae* pv. *lachrymans* resistance score of 3.0. If additionally one mutant allele of a QTL, selected from the QTLs of the invention, was present, the average resistance score of a cucumber plant was 2.5. If additionally two mutant alleles of a QTL, selected from the QTLs of the invention were present, the average score was 2.0. If additionally three mutant alleles of a QTL selected from the QTLs of the invention were present, the average score was 1.5. If additionally four mutant alleles of a QTL, selected from the QTLs of the invention, were present, the average *Pseudomonas syringae* pv. *lachrymans* resistance score was 1.0.

The plant of the invention may be a plant of an inbred line, a hybrid, a doubled haploid, or of a segregating population. As used herein, a plant of an inbred line is a plant of a population of plants that is the result of three or more rounds of selfing, or backcrossing; or which plant is a double haploid. An inbred line may e.g. be a parent line used for the production of a commercial hybrid.

According to an aspect of the invention, the plant is an agronomically elite cucumber plant. The agronomically elite cucumber plant can be an inbred line or a hybrid. In the context of this invention an agronomically elite cucumber plant is a plant having a genotype that as a result of directed crossing and selection by human intervention results in an accumulation of distinguishable and desirable agronomic traits which allows a producer to harvest a product of commercial significance.

As used herein, a hybrid plant is a plant which is the result of a cross between two different plants having different genotypes. More in particular, a hybrid plant is the result of a cross between plants of two different inbred lines, such a hybrid plant may e.g. be a plant of a commercial F1 hybrid variety.

The invention further relates to a cell of a cucumber plant, which cell may comprise a mutant allele of the Gibberellin-20-oxidase gene, and optionally one or more mutant alleles of a QTL selected from the group of QTL2, QTL3, QTL4, QTL5, as defined herein; wherein the mutant allele of the Gibberellin-20-oxidase gene and the mutant alleles of said QTLs confer resistance to *Pseudomonas syringae* pv. *lachrymans*, and are as found in a cucumber plant grown from seed as deposited with NCIMB under accession number NCIMB 42582. The cell comes from a cucumber plant obtainable by crossing a cucumber plant with a cucumber plant grown from seed deposited under accession number NCIMB 42582, and selecting in the obtained F1 and/or the F2 for a cucumber plant that shows resistance to *Pseudomonas syringae* pv. *lachrymans*.

Optionally, one may confirm that said cucumber plant, showing resistance to *Pseudomonas syringae* pv. *lachrymans*, may comprise the mutant allele of the Gibberellin-20-oxidase gene and optionally a mutant allele of a QTL, as defined herein.

The cell may be either in isolated form or may be part of the complete plant or parts thereof.

The cell of the invention may also be a regenerable cell that can be used to regenerate a new plant of the invention. Each cell of a plant of the invention carries the genetic information that leads to resistance to *Pseudomonas syringae* pv. *lachrymans*. The presence of genetic information as used herein is the presence of the mutant allele of the Gibberelline-20-oxidase gene and optionally one or more mutant alleles of a QTL selected from the group of QTL2, QTL3, QTL4, and QTL5 as defined herein.

The invention further relates to the use of a cucumber plant which cucumber plant shows resistance to *Pseudomonas syringae* pv. *lachrymans* as found in a cucumber plant grown from seed as deposited with NCIMB under the accession number NCIMB 42582, as a crop, as a source of seed, as a source of propagating material, or for consumption.

The invention also relates to a cucumber seed which may comprise a mutant allele of the Gibberellin-20-oxidase gene as defined herein, wherein the cucumber plant grown from the seed shows resistance to *Pseudomonas syringae* pv. *lachrymans*. The cucumber seed may additionally comprise one or more mutant alleles of a QTL as defined herein, wherein the cucumber plant grown from the seed shows resistance to *Pseudomonas syringae* pv. *lachrymans*. The seed harbours the mutant allele of the Gibberellin-20-oxidase gene and optionally one or more mutant alleles of a QTL as defined herein, which, when a plant is grown from the seeds, produces a plant of the invention.

The invention also relates to the use of seeds that were deposited with NCIMB under the accession number NCIMB 42582, for transferring resistance to *Pseudomonas syringae* pv. *lachrymans* into another cucumber plant.

The invention further relates to progeny of a cucumber plant or a cucumber seed of the invention, wherein the progeny may comprise a mutant allele of the Gibberelline-20-oxidase gene and optionally one or more mutant alleles of QTL2, QTL3, QTL4, and QTLS as defined herein, and wherein the progeny plant shows resistance to *Pseudomonas syringae* pv. *lachrymans*. Such progeny can be plants, cells, tissues, or seeds. As used herein the term "progeny" is used for the first and all further descendants from a cross with a plant of the invention that may comprise the mutant allele of the Gibberellin-20-oxidase gene and optionally one or more mutant alleles of a QTL selected from the group of QTL2, QTL3, QTL4, and QTLS as defined herein. Progeny also encompasses plants that may comprise the mutant allele of the Gibberellin-20-oxidase gene and optionally one or more mutant alleles of a QTL as defined herein, and are obtained from other plants or progeny of plants of the invention by vegetative propagation. Progeny of the invention comprises the mutant allele of the Gibberellin-20-oxidase gene and optionally one or more mutant alleles of a QTL selected from the group of QTL2, QTL3, QTL4, and QTLS as defined herein and shows resistance to *Pseudomonas syringae* pv. *lachrymans*.

The invention further relates to propagation material capable of developing into and/or being derived from a cucumber plant of the invention, wherein the propagation material is suitable for sexual reproduction, for vegetative reproduction, or suitable for tissue cultures of regenerable cells, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof, wherein the plant developing into and/or produced from the propagation material shows resistance to *Pseudomonas syringae* pv. *lachrymans*.

The invention also relates to a tissue culture of a cucumber plant having resistance to *Pseudomonas syringae* pv. *lachrymans*, which tissue culture may comprise a mutant allele of the Gibberellin-20-oxidase gene, which may comprise a SNP on position 860 of the wild type nucleotide sequence of SEQ ID NO:1 and which tissue culture optionally may comprise one or more mutant alleles of selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

The tissue culture can be made of undifferentiated or already differentiated tissue. Undifferentiated tissues are for example stem tips, anthers, petals, pollen, and can be used in micropropagation to obtain new plantlets that are grown into new plants of the invention. The tissue can also be grown from a cell of the invention.

The invention also relates to a mutant allele of the cucumber Gibberellin-20-oxidase gene as defined herein. In particular, the mutant allele of the Gibberellin-20-oxidase gene may comprise a SNP on position 860 of the wild type nucleotide sequence of SEQ ID NO: 1. In one embodiment of the invention, the SNP may comprise a change from guanine to adenine. In one embodiment of the invention, the nucleic acid sequence of the mutant allele of the Gibberellin-20-oxidase gene may comprise SEQ ID NO: 2.

The mutant allele of the Gibberellin-20-oxidase gene of the invention is not known in the art to occur in nature. In one embodiment, the gene is an isolated gene. The gene can also be present in the genome of a cucumber plant to confer resistance against *Pseudomonas syringae* pv. *lachrymans* to that plant.

The sequences of SEQ ID NO:1 and SEQ ID NO:2, as can be found in Table 1, are both coding sequences of the cucumber Gibberellin-20-oxidase gene. The only difference between the two sequences is the SNP on position 860 of the SEQ ID NO:1. The sequence SEQ ID NO:2 is the mutant allele of the Gibberellin-20-oxidase gene.

The mutant allele of the Gibberellin-20-oxidase gene of the invention can be introduced into a plant by introgressing the mutant allele of the Gibberellin-20-oxidase gene from a plant which may comprise the mutant allele of the Gibberellin-20-oxidase gene into another plant through crossing and selecting. The mutant allele of the Gibberellin-20-oxidase gene of the invention can also be introduced into a plant by means of genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

Techniques that can suitably be used for modification of a gene or a combination of genes, may comprise general plant transformation techniques, such as the use of an *Agrobacterium*-mediated transformation method. Other genome editing methods such as the use of a CRISPR/Cas system might also be employed. Methods of genetic modification are well known to a person skilled in the art.

The invention further relates to a mutant Gibberellin-20-oxidase protein, which may comprise a substitution on position 287 of the wild type amino acid sequence of SEQ ID NO:3. In particular, the mutant Gibberellin-20-oxidase protein may comprise SEQ ID NO:4.

The sequences SEQ ID NO:3 and SEQ ID No:4, as can be found in Table 1, are both amino acid sequences of the cucumber Gibberellin-20-oxidase gene. The only difference between the two sequences is the amino acid change on position 287 of the SEQ ID NO:3. The sequence SEQ ID NO:4 is the mutant amino acid sequence of the Gibberellin-20-oxidase gene. The invention further relates to nucleic acid sequences which can be used as markers for the identification of the resistance conferring alleles of the QTLs as defined herein.

The marker for identification of the mutant allele of QTL2 is SEQ ID NO:8. The marker for identification of the mutant allele of QTL3 is SEQ ID NO:14. The marker for identification of the mutant allele of QTL4 is SEQ ID NO:26. The marker for identification of the mutant allele of QTL5 is SEQ ID NO:32. Any sequence that is derived from said sequences which may comprise the SNP that is correlated with the trait of resistance to *Pseudomonas syringae* pv. *lachrymans* is also part of the current invention.

The invention further relates to the use of the mutant allele of the Gibberellin-20-oxidase gene and/or any of the above-mentioned markers, or a part thereof, for identifying and/or developing a cucumber plant showing resistance to *Pseudomonas syringae* pv. *lachrymans*. The sequences SEQ ID NO:8, SEQ ID NO:14, SEQ ID NO:26, and SEQ ID NO:32 are linked with the *Pseudomonas syringae* pv. *lachrymans* resistance conferring alleles of QTL2, QTL3, QTL4, and QTL5 respectively. The sequences SEQ ID NO:8, SEQ ID NO:14, SEQ ID NO:26, and SEQ ID NO:32 only differ from their wild type sequence counterparts SEQ ID NO:7, SEQ ID NO:13, SEQ ID NO:25, and SEQ ID NO:31, that are linked with the susceptible alleles of the mentioned QTLs, by only one SNP each, as indicated in Table 2.

The mutant allele of the Gibberelline-20-oxidase gene and optionally one or more mutant alleles of the QTLs as defined herein, as found in seeds that were deposited under accession number NCIMB 42582, may be used for conferring resistance to *Pseudomonas syringae* pv. *lachrymans* in a cucumber plant.

The invention also relates to a method for identifying a cucumber plant showing resistance to *Pseudomonas syringae* pv. *lachrymans* which may comprise:

a) detecting in a cucumber plant a SNP in the wild type nucleotide sequence of SEQ ID NO:1, thereby identifying a cucumber plant showing resistance to *Pseudomonas syringae* pv. *lachrymans*;

b) optionally performing a phenotypical assay for *Pseudomonas syringae* pv. *lachrymans* resistance, to confirm that the cucumber plant is resistant to *Pseudomonas syringae* pv. *lachrymans*.

In particular, the SNP in the wild type nucleotide sequence of SEQ ID NO:1 is a change from guanine (G) to adenine (A) on position 860.

The method for identifying a cucumber plant showing resistance to *Pseudomonas syringae* pv. *lachrymans* may further comprise detecting one or more mutant alleles of a QTL selected from the group consisting of QTL2, QTL3, QTL4, QTL5, as defined herein.

Detecting plants having the trait of resistance to *Pseudomonas syringae* pv. *lachrymans* is done by using the sequence SEQ ID NO:2 of the Gibberellin-20-oxidase gene and optionally by using one or more of the marker sequences selected from the group consisting of marker M5009, represented by SEQ ID NO:8, marker M2071, represented by SEQ ID NO:14, marker M5644, represented by SEQ ID NO:26, and marker M5618, represented by SEQ ID NO:32.

The invention relates to a method of selecting a cucumber plant for showing resistance to *Pseudomonas syringae* pv. *lachrymans* which may comprise: a) assaying genomic nucleic acids of a cucumber plant for the presence of a mutation in the allele of the Gibberellin-20-oxidase gene, wherein the SNP in the Gibberelline-20-oxidase gene is located on position 860 of the wild type nucleotide sequence SEQ ID NO:1; b) determining whether said mutation is homozygous or heterozygous; c) and selecting said cucumber plant based on said determination.

The invention further relates to a method of selecting for a plant for showing resistance to *Pseudomonas syringae* pv. *lachrymans*, which may comprise: a) assaying genomic nucleic acids of a cucumber plant for the presence of a mutation in the allele of the Gibberellin-20-oxidase gene, wherein the SNP in the Gibberelline-20-oxidase gene is located on position 860 of the wild type nucleotide sequence SEQ ID NO:1, and additionally for the presence of one or more mutant alleles of a QTL selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618; b) determining whether said mutation and said mutant allele is homozygous or heterozygous; c) and selecting said cucumber plant based on said determination.

The invention further relates to a method for producing a hybrid cucumber seed, wherein a plant grown from such seed shows resistance to *Pseudomonas syringae* pv. *lachrymans*, said method which may comprise crossing a first parent plant with a second parent plant and harvesting the resultant seed, wherein said first parent plant and/or said second parent plant may comprise a mutant allele of the Gibberellin-20-oxidase gene as defined herein, wherein the mutant allele of the Gibberellin-20-oxidase gene confers resistance to *Pseudomonas syringae* pv. *lachrymans* in a plant grown from the seed.

It is clear that the parent plant which may comprise the mutant allele of the Gibberellin-20-oxidase gene can be, but is not necessarily, a plant grown directly from the deposited seeds. The parent plant can also be a progeny plant from the deposited seed, a progeny plant derived therefrom, or a progeny plant from seeds that have obtained the mutant allele of the Gibberellin-20-oxidase gene and optionally one or more mutant alleles of a QTL of the invention by other means.

In an embodiment of the invention, said first parent plant and/or said second parent plant additionally may comprise one or more mutant alleles of a QTL as defined herein. The resulting plant that may comprise the mutant allele of the Gibberellin-20-oxidase and optionally one or more mutant alleles of a QTL selected from the group consisting of QTL2, QTL3, QTL4, and QTL5 as defined herein, and which shows resistance to *Pseudomonas syringae* pv. *lachrymans*, is also a plant of the invention.

The invention further relates to a method for producing a hybrid cucumber plant that may comprise the mutant allele of the Gibberellin-20-oxidase gene and optionally one or more mutant alleles of a QTL as defined herein and wherein the hybrid cucumber plant shows resistance to *Pseudomonas syringae* pv. *lachrymans* which may comprise crossing a first parent cucumber plant with a second parent cucumber plant and harvesting the resultant hybrid seed, of which the first parent plant and/or the second parent plant may comprise the mutant allele of the Gibberellin-20-oxidase gene and optionally one or more mutant alleles of a QTL selected from the group consisting of QTL2, QTL3, QTL4, and QTL5 as defined herein and shows resistance to *Pseudomonas syringae* pv. *lachrymans*, and growing said hybrid seeds into hybrid plants that may comprise the mutant allele of the Gibberellin-20-oxidase gene and optionally one or more mutant alleles of a QTL as defined herein, and show resistance to *Pseudomonas syringae* pv. *lachrymans*.

The invention also relates to a method for producing a cucumber plant which shows resistance to *Pseudomonas syringae* pv. *lachrymans*, wherein the method may comprise:

a) crossing a plant which may comprise a mutant allele of the Gibberelline-20-oxidase gene and optionally one or more mutant alleles of a QTL selected from the group consisting of QTL2, QTL3, QTL4 and QTL5, as defined herein, with another plant to obtain an F1 population;

b) optionally performing one or more rounds of selfing and/or crossing a plant from the F1 to obtain a further generation population;

c) selecting from the population a plant that may comprise a mutant allele of the Gibberellin-20-oxidase gene and optionally one or more mutant alleles of a QTL selected from the group consisting of QTL2, QTL3, QTL4 and QTL5 as defined herein, and wherein the selected plant shows resistance to *Pseudomonas syringae* pv. *lachrymans*, and/or selecting from the population a plant showing resistance to *Pseudomonas syringae* pv. *lachrymans* in a phenotypical assay. The method for producing a cucumber plant which shows resistance to *Pseudomonas syringae* pv. *lachrymans* may further comprise the step of crossing the selected plant with a plant which may comprise a mutant allele of the Gibberelline-20-oxidase gene and optionally one or more mutant alleles of a QTL as defined herein; and repeating said steps a) to c).

In the course of breeding a new cucumber plant carrying the mutant allele of the Gibberellin-20-oxidase gene and optionally one or more mutant alleles of a QTL of the invention desirable agronomic traits may be introduced into said cucumber plant independently of the mutant allele of the gene and the optionally one or more mutant alleles of a QTL of the invention.

As used herein, "desirable traits" include but are not limited to e.g. improved yield, fruit shape, fruit size, fruit colour, seed size, plant vigour, plant height, and resistance to one or more diseases or disease causing organisms. Any one of these desirable traits may be combined with the mutant allele of the gene and optionally one or more mutant alleles of a QTL of the invention.

A skilled person is familiar with introducing a new trait into a plant already possessing other desired agricultural properties, for instance by means of introgression.

Introgression can be done by means of standard breeding techniques, wherein selection can be done either phenotypically or with the use of (molecular) markers or a combination thereof.

The invention thus provides a method of introducing another desired trait into a cucumber plant which has the trait of resistance to *Pseudomonas syringae* pv. *lachrymans*, which may comprise: a) crossing a cucumber plant that has the trait of resistance to *Pseudomonas syringae* pv. *lachrymans*, representative seed of which were deposited under deposit number NCIMB 42582, with a second cucumber plant that may comprise a desired trait to produce F1 progeny; b) selecting an F1 progeny that may comprise the trait of resistance to *Pseudomonas syringae* pv. *lachrymans* and the desired trait; c) crossing the selected F1 progeny with either parent, to produce backcross progeny; d) selecting backcross progeny which may comprise the desired trait and the trait of resistance to *Pseudomonas syringae* pv. *lachrymans*; and e) optionally repeating steps c) and d) one or more times in succession to produce selected fourth or higher backcross progeny that may comprise the desired trait and the trait of resistance to *Pseudomonas syringae* pv. *lachrymans*. The invention also includes a cucumber plant produced by this method.

The invention further provides a method for the production of a cucumber plant having the trait of resistance to *Pseudomonas syringae* pv. *lachrymans* by using a doubled haploid generation technique to generate a doubled haploid line which may comprise the said trait.

The invention also relates to a method for the production of a cucumber plant having the trait of resistance to *Pseudomonas syringae* pv. *lachrymans* which may comprise using a seed that may comprise the mutant allele of the Gibberellin-20-oxidase gene and optionally one or more mutant alleles of a QTL as defined herein in its genome that leads to the trait of resistance to *Pseudomonas syringae* pv. *lachrymans* for growing the said cucumber plant. The seeds are suitably seeds of which a representative sample was deposited with the NCIMB under deposit number NCIMB 42582.

The invention relates to a method for producing a cucumber plant having resistance to *Pseudomonas syringae* pv. *lachrymans* which may comprise the steps of: a) introducing mutations in a population of cucumber plants; b) selecting a cucumber plant showing resistance to *Pseudomonas syringae* pv. *lachrymans*; c) verifying if the plant selected under step b) has a mutation in a allele of the Gibberellin-20-oxidase gene, wherein the mutation is a SNP in the Gibberelline-20-oxidase gene and is located on position 860 of the wild type nucleotide sequence SEQ ID NO:1, and selecting a plant which may comprise such a mutation; and d) growing the plants obtained under step c). Mutations in plants can be induced by many different methods such as TILLING, EMS and ZFN. The skilled person knows how to and which method to implement.

The invention also relates to a method for seed production which may comprise growing cucumber plants from seeds of which a representative sample was deposited with the NCIMB under deposit number NCIMB 42582, allowing the plants to produce seeds, and harvesting those seeds. The seeds produced may comprise the mutant allele of the Gibberellin-20-oxidase gene and optionally one or more mutant alleles of a QTL as defined herein and a plant grown from the seed shows resistance to *Pseudomonas syringae* pv. *lachrymans*. Production of the seeds is suitably done by crossing and/or selfing.

In an embodiment, the invention relates to a method for the production of a cucumber plant having the trait of resistance to *Pseudomonas syringae* pv. *lachrymans* by using tissue culture.

The invention furthermore relates to a method for the production of a cucumber plant having the trait of resistance to *Pseudomonas syringae* pv. *lachrymans* by using vegetative reproduction.

In a further embodiment, the invention relates to a method for the production of a cucumber plant having the trait of resistance to *Pseudomonas syringae* pv. *lachrymans*, wherein progeny or propagation material of a plant which may comprise the mutant allele of the Gibberellin-20-oxidase gene and optionally one or more mutant alleles of a QTL as defined herein, causing the trait of the invention, is used as a source to introgress the trait into another cucumber plant.

Representative seed of a plant which may comprise the mutant allele of the Gibberellin-20-oxidase gene and the mutant alleles of a QTL as defined herein was deposited under deposit number NCIMB 42582.

The invention also relates to a breeding method for the development of cucumber plants which may comprise the mutant allele of the Gibberellin-20-oxidase gene and optionally one or more mutant alleles of a QTL as defined herein, which cucumber plants have the trait of resistance to *Pseudomonas syringae* pv. *lachrymans*, wherein germplasm which may comprise the mutant allele of the Gibberellin-20-oxidase gene and optionally one or more mutant alleles of a QTL as defined herein, is used.

The invention provides preferably a cucumber plant having the trait of resistance to *Pseudomonas syringae* pv. *lachrymans* of the invention, which plant is obtainable by any of the methods herein described and/or any method familiar to the skilled person.

The sequences of SEQ ID NO:1 and SEQ ID NO:3 as shown in Table 1 represent the wildtype allele of the Gibberellin-20-oxidase gene and the wildtype sequence of the Gibberellin-20-oxidase protein respectively, as present in cucumber plants susceptible to *Pseudomonas syringae* pv. *lachrymans*. The sequences of SEQ ID NO:2 and SEQ ID NO:4 as shown in Table 1 represent the mutant allele of the Gibberellin-20-oxidase gene and the mutant Gibberellin-20-oxidase protein respectively, that in the genome of seeds of the deposit NCIMB 42582 are linked to resistance to *Pseudomonas syringae* pv. *lachrymans*.

In the Gibberellin-20-oxidase gene sequences, the nucleotide that is different between the mutant allele (SEQ ID NO:2) conferring resistance to *Pseudomonas syringae* pv. *lachrymans* and the wildtype allele (SEQ ID NO:1) is in bold and between square brackets. This nucleotide is a SNP on position 860, wherein SEQ ID NO:1 has a G and SEQ ID NO:2 has an A.

In the Gibberellin-20-oxidase protein sequences, the amino acid that is different between the mutant protein (SEQ ID NO:4) conferring resistance to *Pseudomonas syringae* pv. *lachrymans* and the wildtype protein (SEQ ID NO:3) is in bold and between square brackets. This amino acid is polymorph on position 287, wherein SEQ ID NO:3 has a C and SEQ ID NO:4 has an Y.

The SNPs indicated in these sequences (the nucleotides in bold and between square brackets) may be used as molecular markers for detecting the presence of the mutant allele of the Gibberellin-20-oxidase gene in the progeny of a cross between a plant not comprising the resistance to *Pseudomonas syringae* pv. *lachrymans* and a plant which may comprise said resistance, which plant may be a plant grown from seeds of which a representative sample was under NCIMB accession number 42582.

The sequences SEQ ID NO:8, SEQ ID NO:14, SEQ ID NO:26, SEQ ID NO:32, as shown in Table 2, represent the sequences of markers M5009, M2071, M5644, and M5618 respectively, that are linked to the resistance conferring alleles of QTL2, QTL3, QTL4 and QTL5 respectively, as present in the genome of seeds of the deposit NCIMB 42582.

The sequences of SEQ ID NO:7, SEQ ID NO:13, SEQ ID NO:25, SEQ ID NO:31, as shown in Table 2, represent the sequences of markers M5009, M2071, M5644 and M5618 respectively, that are linked to wildtype susceptible alleles of QTL2, QTL3, QTL4 and QTL5 respectively, as present in cucumber plants susceptible to *Pseudomonas syringae* pv. *lachrymans*.

As shown in Table 2, the nucleotides that are different between the two sequences of each marker are in bold and between square brackets.

For the marker M5009 this is a SNP on position 101, wherein SEQ ID NO:7 on position 101 has a T and SEQ ID NO:8 on position 101 has an C.

For the marker M2071 this is a SNP on position 101, wherein SEQ ID NO:13 on position 101 has a C and SEQ ID NO:14 on position 101 has an A.

For the marker M5644 this is a SNP on position 101, wherein SEQ ID NO:25 on position 101 has an A and SEQ ID NO:26 on position has a C.

For the marker M5618 this is a SNP on position 101, wherein SEQ ID NO:31 on position 101 has a G and SEQ ID NO:32 on position 101 has an T.

The SNPs indicated in these sequences (the nucleotides in bold and between square brackets) may be used as molecular markers for detecting the presence of the resistance conferring alleles of QTL2, QTL3, QTL4 and QTL5 respectively, in the progeny of a cross between a plant not comprising the resistance to *Pseudomonas syringae* pv. *lachrymans* and a plant which may comprise said resistance, which plant may be a plant grown from seeds of which a representative sample was under NCIMB accession number 42582.

TABLE 1

The nucleotide sequences and amino acid sequences of the cucumber wild type Gibberellin-20-oxidase (GAOX2) gene and the mutant, mutant allele of the Gibberellin-20-oxidase (GAOX2) gene. The nucleotides and amino acids between brackets and in bold indicate the SNPs.

| Name | SEQ ID Number | Sequence |
|---|---|---|
| Gibberellin-20-oxidase (GAOX2) gene | SEQ ID NO: 1 Wild type | ATGGAATCGACGACGACGGTGGGGAGGGTGGCCGGA ATAATATTGCCGACGATGGTAGACAAGAAGAAGAAA CTACCAAGGGAATTCGTGTGGCCACGAGGGGAGTTG GCAGGGGAGGAAAGAGGGGAGTTGAAAGAGCCGTT GATAGACTTAGGGGGATTCAGGAGAGGGGAGGAAGA GGCGACGGCGGAGGCGGCGGCGATGGTGAGGATGGC ATGTATGAAACATGGGGTGTTTCAGGTGACGAATCAC GGAGTGGAAGAGGAGCTGATAAAGGCGGCGTATGAA GAAGGGGAGGGGATATTTAAGATGCCATTAGTGAAG AAAATAAGCGTGGGGAAAAAACCGGGGAGAGTGTCG GGATATTCAGGAGCTCATGCAGATAGAATTCTCTTCAA AACTTCCATGGAAAGAGACCTTCTCTTTTGAGTATTC TAATGATGATTCTCAACCTCTACATGTTCTTCATCACT TTAAATCATTGTTCGGTTGCGACTTCGAGAATACTGG ATGGGTATACCAAAGATACTGTGAAGAAATGACAAG AACAGCATTAATGATAATGGAGCTTCTAGCAATAAGT TTGGGAGTAGAGAGATATCATTACAGGAAGTTCTTTG AAGATGGAAAGTCAATAATGAGATGCAATTACTATC CACCATGTGAGAATGCAAGCCTGACTTTAGGCACAG GCCCTCATTGTGACCCAACTTCACTCACTATTCTCCAT CAAGATCAAGTTGGTGGCCTTGAAGTTTTTGCTAACA ACGCTTGGCTCTCTGTCAAACCTAGACCTGATGCTTT GGTTATTAACATTGGTGACACTTTTATGGCACTGTCG |

TABLE 1-continued

The nucleotide sequences and amino acid sequences of the cucumber wild type Gibberellin-20-oxidase (GAOX2) gene and the mutant, mutant allele of the Gibberellin-20-oxidase (GAOX2) gene. The nucleotides and amino acids between brackets and in bold indicate the SNPs.

| Name | SEQ ID Number | Sequence |
|---|---|---|
| | | AATGGAGCGTACAAGAGCT[G]TCTGCATAGGGCAGT GGTGAACAGGAAGAGAGAGAGAAGGTCATTGGTGTT CTTTGTGTGCCCAAAAGATGATAAAGTGGTGAGACCC CCACAAGATTTGGTGGGCAGAGAAGGGCCAAGACAG TACCCTGATTTCACATGGTCAGAGCTTTTGGAGTTTA CACAAAAACATTACAGAGCTGATGTTGCTACACTCCA AAGCTTTGTCCACTGGCTTCAAGCTAAACCTCACCCT CCAAAAATTCCATTTTAA |
| | SEQ ID NO: 2 Resistance conferring mutant | ATGGAATCGACGACGACGGTGGGGAGGGTGGCCGGA ATAATATTGCCGACGATGGTAGACAAGAAGAAGAAA CTACCAAGGGAATTCGTGTGGCCACGAGGGGAGTTG GCAGGGGAGGAAAGAGGGGAGTTGAAAGAGCCGTT GATAGACTTAGGGGGATTCAGGAGAGGGGAGGAAGA GGCGACGGCGGAGGCGGCGGCGATGGTGAGGATGGC ATGTATGAAACATGGGGTGTTTCAGGTGACGAATCAC GGAGTGGAAGAGGAGCTGATAAAGGCGGCGTATGAA GAAGGGGAGGGGATATTTAAGATGCCATTAGTGAAG AAAATAAGCGTGGGGAAAAAACCGGGGAGAGTGTCG GGATATTCAGGAGCTCATGCAGATAGATTCTCTTCAA AACTTCCATGGAAAGAGACCTTCTCTTTTGAGTATTC TAATGATGATTCTCAACCTCTACATGTTCTTCATCACT TTAAATCATTGTTCGGTTGCGACTTCGAGAATACTGG ATGGGTATACCAAAGATACTGTGAAGAAATGACAAG AACAGCATTAATGATAATGGAGCTTCTAGCAATAAGT TTGGGAGTAGAGAGATATCATTACAGGAAGTTCTTTG AAGATGGAAAGTCAATAATGAGATGCAATTACTATC CACCATGTGAGAATGCAAGCCTGACTTTAGGCACAG GCCCTCATTGTGACCCAACTTCACTCACTATTCTCCAT CAAGATCAAGTTGGTGGCCTTGAAGTTTTTGCTAACA ACGCTTGGCTCTCTGTCAAACCTAGACCTGATGCTTT GGTTATTAACATTGGTGACACTTTTATGGCACTGTCG AATGGAGCGTACAAGAGCT[A]TCTGCATAGGGCAGT GGTGAACAGGAAGAGAGAGAGAAGGTCATTGGTGTT CTTTGTGTGCCCAAAAGATGATAAAGTGGTGAGACCC CCACAAGATTTGGTGGGCAGAGAAGGGCCAAGACAG TACCCTGATTTCACATGGTCAGAGCTTTTGGAGTTTA CACAAAAACATTACAGAGCTGATGTTGCTACACTCCA AAGCTTTGTCCACTGGCTTCAAGCTAAACCTCACCCT CCAAAAATTCCATTTTAA |
| Gibberelline-20-oxidase amino acid sequence | SEQ ID NO: 3 Wild type | MESTTTVGRVAGIILPTMVDKKKKLPREFVWPRGELAG EERGELKEPLIDLGGFRRGEEEATAEAAAMVRMACMK HGVFQVTNHGVEEELIKAAYEEGEGIFKMPLVKKISVG KKPGRVSGYSGAHADRFSSKLPWKETFSFEYSNDDSQP LHVLHHFKSLFGCDFENTGWVYQRYCEEMTRTALMIM ELLAISLGVERYHYRKFFEDGKSIMRCNYYPPCENASLT LGTGPHCDPTSLTILHQDQVGGLEVFANNAWLSVKPRP DALVINIGDTFMALSNGAYKS[C]LHRAVVNRKRERRSL VFFVCPKDDKVVRPPQDLVGREGPRQYPDFTWSELLEF TQKHYRADVATLQSFVHWLQAKPHPPKIPF |
| | SEQ ID NO: 4 Resistance conferring mutant | MESTTTVGRVAGIILPTMVDKKKKLPREFVWPRGELAG EERGELKEPLIDLGGFRRGEEEATAEAAAMVRMACMK HGVFQVTNHGVEEELIKAAYEEGEGIFKMPLVKKISVG KKPGRVSGYSGAHADRFSSKLPWKETFSFEYSNDDSQP LHVLHHFKSLFGCDFENTGWVYQRYCEEMTRTALMIM ELLAISLGVERYHYRKFFEDGKSIMRCNYYPPCENASLT LGTGPHCDPTSLTILHQDQVGGLEVFANNAWLSVKPRP DALVINIGDTFMALSNGAYKS[Y]LHRAVVNRKRERRSL VFFVCPKDDKVVRPPQDLVGREGPRQYPDFTWSELLEF TQKHYRADVATLQSFVHWLQAKPHPPKIPF |

TABLE 2

Sequences of flanking markers indicating the location of the QTLs linked to *Pseudomonas syringae* pv. *lachrymans* resistance and sequences of markers linked to the QTLs linked to *Pseudomonas syringae* pv. *lachrymans* resistance. The nucleotides in bold and between square brackets indicate the SNPs.

| Marker name | SEQ ID Number | Sequence |
|---|---|---|
| M5007 | SEQ ID NO: 5 | TTGAAAAATTAAATCTTCTsTATGATATTATCCGCTGTAAATCTAT CCTTAATAAGCATTAGAACTGTATTTGTTCTTTTATAAAAAAAAA ATCTAACTC[T]TTCCAATTTATTTAAAAAAAGTACATTCTCTATC TACTATCATTTTGTTTGTCTATCACCCACCCCTCCCTACCTTCATC CTCAGATAGCATCTTCTyGC |
| | SEQ ID NO: 6 | TTGAAAAATTAAATCTTCTsTATGATATTATCCGCTGTAAATCTAT CCTTAATAAGCATTAGAACTGTATTTGTTCTTTTATAAAAAAAAA ATCTAACTC[A]TTCCAATTTATTTAAAAAAAGTACATTCTCTATC TACTATCATTTTGTTTGTCTATCACCCACCCCTCCCTACCTTCATC |
| M5009 | SEQ ID NO: 7 | TTTATTTCATAATTTCTATCTATTTAGTTCACAAATTTTAATAAAT TCTTTCAATTTTATCTAACTTATTCATGCATTAAAATAAACATTTA ACGTTGAA[T]CAATATAGAATAyAACAATTTGTTATAGAAAGCTT TCAATATGTCAGTATTAGCTTTTAATTAATCGATTAGACTTGTAA |
| | SEQ ID NO: 8 | TTTATTTCATAATTTCTATCTATTTAGTTCACAAATTTTAATAAAT TCTTTCAATTTTATCTAACTTATTCATGCATTAAAATAAACATTTA ACGTTGAA[C]CAATATAGAATAyAACAATTTGTTATAGAAAGCT TTCAATATGTCAGTATTAGCTTTTAATTAATCGATTAGACTTGTA |
| M5609 | SEQ ID NO: 9 | TTCTATTTTAATATTATTTATTTATCGATATAGGTCATGAATGCG ACCAAAATCTCACACTTGAGACTACATCTCACTAAAAGACCGTA GATAAAATAA[A]GTATATGTGTAGTATTTCTCATTGGTAGAGAC GTTTTTGACAAAACCAAAGGCAAAGTCTACTACATCAATTTGA |
| | SEQ ID NO: 10 | TTCTATTTTAATATTATTTATTTATCGATATAGGTCATGAATGCG ACCAAAATCTCACACTTGAGACTACATCTCACTAAAAGACCGTA GATAAAATAA[G]GTATATGTGTAGTATTTCTCATTGGTAGAGAC GTTTTTGACAAAACCAAAGGCAAAGTCTACTACATCAATTTGA |
| M1000 | SEQ ID NO: 11 | TTAACCAAACCAGATTCTGTCTCTCGTGACATAGAATTAGATCTT CACCTCATTCAAAATGGTCTGCATCGGACATCACGTTTCGAGATT GCAATGCAAGTGGTTCGGAACATGGTTGCTACTGTTGGTGACTC GAATGTCTGGTTAGCTGGCCATTCCCTTGGATCCGCCATGGCAAT |
| | SEQ ID NO: 12 | TTAACCAAACCAGATTCTGTCTCTCGTGACATAGAATTAGATCTT CACCTCATTCAAAATGGTCTGCATCGGACATCACGTTTCGAGATT GCAATGCAAGTGGTTCGGAACATGGTTGCTACTGTTGGTGACTC GAATGTCTGGTTAGCTGGCCATTCCCTTGGATCCGCCATGGCAAT GCTTGCTGGAAGAACCATGGCAAGAAC[G]GGCATTTTCCTCAAA TCATACCTCTTCAATCCTCCATTCTTGGC |
| M2071 | SEQ ID NO: 13 | AACCACCATTTGTCCCCATCTAGAGCTATTTACTCCGATAGATTC ATACCCAGTAGATCTGGTTCTAATTTTGCCCTTTTTGATATCTCCC CTGTTTCCA[C]TTCCCACTCTGATGGTCGTGAGGATACTTCTACT GCTTACGCTACCCTTCTTCGTACTGCTTTGTTTGGTCCTGATTCTG GTGTAATCCCTCCTGCTACT |
| | SEQ ID NO: 14 | AACCACCATTTGTCCCCATCTAGAGCTATTTACTCCGATAGATTC ATACCCAGTAGATCTGGTTCTAATTTTGCCCTTTTTGATATCTCCC CTGTTTCCA[A]TTCCCACTCTGATGGTCGTGAGGATACTTCTACT GCTTACGCTACCCTTCTTCGTACTGCTTTGTTTGGTCCTGATTCTG GTGTAATCCCTCCTGCTACT |
| M3418 | SEQ ID NO: 15 | CAACAAAAAAGTGGACTTCATTTCTAAGCTAGGCATCGAATATA AAACAAGCACTAAACAAATTGATAGAATCACTAGATAATCAAGC TAACTAAAATACGGG[A]GAATACGTACCTTAATATGAGCCTATC CCAGTCATAAAACCCTGCATTTATCAAATTCCGTGTTGTACATTC CCTCTGCTTTTCGCTTCTTCCAGT |
| | SEQ ID NO: 16 | CAACAAAAAAGTGGACTTCATTTCTAAGCTAGGCATCGAATATA AAACAAGCACTAAACAAATTGATAGAATCACTAGATAATCAAGC TAACTAAAATACGGG[G]GAATACGTACCTTAATATGAGCCTATC CCAGTCATAAAACCCTGCATTTATCAAATTCCGTGTTGTACATTC |
| M1520 | SEQ ID NO: 23 | ATCAGTAAGGTAAAGATTTGGTTAAAGTGTTTATTTAACGCATTT GCAATCCATTTGAGTTGACATGGTCTGATGCAAAACATTCTTGTGC TCGAGCATATAAAAAAGAGAGGTAAATCTCACCTGCGACATCGA CTTGTTTGCTCGGGCTAGCCGAAACACATTTAACATACAATAAA ACACAGAGTACACAATATGATTTCCAAAAGTATATATGCTAACT TAAATATTATTTGACTCTGGTACATCACAATGTTGTCAAAGTTCA TGAATGCACTTTCCACTGATGAAATCTATAACTTTTGTAACTGCT TGATCCAGTGCAGCAGAGACTGTAGCTAGAATTCTGCAAGAATTC TTC[G]GCAGTTGGTTTTTCGCCATCTACGATATCGTTACAGCTTT TAGAAAATATGGCAGGAACTTTGAATATATCAGCCACATAGGCTA CTGCTGCTCCCTCCATATCTTTAACTGTGGCATCATTAGCTACAA |

TABLE 2-continued

Sequences of flanking markers indicating the location of the QTLs linked to *Pseudomonas syringae* pv. *lachrymans* resistance and sequences of markers linked to the QTLs linked to *Pseudomonas syringae* pv. *lachrymans* resistance. The nucleotides in bold and between square brackets indicate the SNPs.

| Marker name | SEQ ID Number | Sequence |
|---|---|---|
| | | TCGATGATTCATCTTGTGCAGACATGTCTAGTGAATCACCCGTTG ATAATTTGCCAACCTTTAGATCAAGTTCCTTATGGAGATTGGGCG TTTTCCATGCTTGCTTCAATCCGACTCCATATAAATCAAAAACTG GAATAGGTATACGTCTGTCATGGAAGGCACACTCGGGATACCGA GAACACGTCG |
| | SEQ ID NO: 24 | ATCAGTAAGGTAAAGATTTGGTTAAAGTGTTTATTTAACGCATTT GCAATCCATTTGAGTTGACATGGTCTGATGCAAAACATCTTGTGC TCGAGCATATAAAAAAGAGAGGTAAATCTCACCTGCGACATCGA CTTGTTTGCTCGGGCTAGCCGAAACACATTTAACATACAATAAA ACACAGAGTACACAATATGATTTCCAAAAGTATATATGCTAACT TAAATATTATTTGACTCTGGTACATCACAATGTTGTCAAAGTTCA TGAATGCACTTTCCACTGATGAAATCTATAACTTTTGTAACTGCT TGATCCAGTGCAGCAGAGACTGTAGCTAGATTCTGCAAGAATTC TTC[A]GCAGTTGGTTTTTCGCCATCTACGATATCSGTTACAGCTTT TAGAAATATGGCAGGAACTTTGAATATATCAGCCACATAGGCTA CTGCTGCTCCCTCCATATCTTTAACTGTGGCATCATTAGCTACAA TCGATGATTCATCTTGTGCAGACATGTCTAGTGAATCACCCGTTG |
| M5644 | SEQ ID NO: 25 | CTGTAAACCTTGAGAGGAGGTAAAAAAGATAAGTCAATTTTTCA TTTTTCAAAACAACTTTCGTTGAGAAAAAATGAAAGAATAGAGC ATACAAAGGGAG[A]TCAGCTAAAATTAGGGGCTCCAACTATACA AGACAAAAAGTCAAATTCAGGTCACAGAAATACGCAAAGAAGA AAACATGTCCTCAATGCCAAATACATC |
| | SEQ ID NO: 26 | CTGTAAACCTTGAGAGGAGGTAAAAAAGATAAGTCAATTTTTCA TTTTTCAAAACAACTTTCGTTGAGAAAAAATGAAAGAATAGAGC ATACAAAGGGAG[C]TCAGCTAAAATTAGGGGCTCCAACTATACA AGACAAAAAGTCAAATTCAGGTCACAGAAATACGCAAAGAAGA AAACATGTCCTCAATGCCAAATACATC |
| M0459 | SEQ ID NO: 27 | AAGCTTCAACTTTTTCTTTTTTTTTTGTTTCATTTTCGCTCTTAA ATTATGCTTCACAAAATGGAAAATACTTTATGAATGGGAAGGTA AAAGAAGAA[C]AATCTTGAGACATGAACTATGTGAAAATAATTT TTTTAAAAAAATGGTATTTCTTTTCTTAATAAACCATTACTTTCCA CTCTGGATAGCAGTGTACTT |
| | SEQ ID NO: 28 | AAGCTTCAACTTTTTCTTTTTTTTTTGTTTCATTTTCGCTCTTAA ATTATGCTTCACAAAATGGAAAATACTTTATGAATGGGAAGGTA AAAGAAGAA[G]AATCTTGAGACATGAACTATGTGAAAATAATTT TTTTAAAAAAATGGTATTTCTTTTCTTAATAAACCATTACTTTCCA CTCTGGATAGCAGTGTACTT |
| M5843 | SEQ ID NO: 29 | AATCTATCACTTTGTCACCTGTTTTTGTGAAGCCTGATTGTATTTT GTTGATATCTGCTTTTCGTTAGGTTTTTTTAAGATCAAGTAAAAT TGTACCATTAAACTGCTTGCATCTCTCATCTGTAG[G]CAGCAGAA GATTTTTTGGTTCACCTATTTGAAGATACCATGCTGTGTGCTATT CATGCCAAACGTGTAACTATCAGTAAGTCAATCTTCACATATTTG AGTTTTGTTCCAATTTTGATTATGGTAGCTATTT |
| | SEQ ID NO: 30 | AATCTATCACTTTGTCACCTGTTTTTGTGAAGCCTGATTGTATTTT GTTGATATCTGCTTTTCGTTAGGTTTTTTTAAGATCAAGTAAAAT TGTACCATTAAACTGCTTGCATCTCTCATCTGTAG[A]CAGCAGAA GATTTTTTGGTTCACCTATTTGAAGATACCATGCTGTGTGCTATT CATGCCAAACGTGTAACTATCAGTAAGTCAATCTTCACATATTTG AGTTTTGTTCCAATTTTGATTATGGTAGCTATTT |
| M5618 | SEQ ID NO: 31 | TCTATTTTTAAAAAATTGAAGTAAAATCCAAATTCATGTCATAC AGTTCAATCTCAAATTATGAAAATTTGTTGTATTAGTTTTGAGTT CAATATCAAA[G]TTAAGTAAATTTGAAAAGTAAAAGGTATTTGA AAyAAAAATTGTTATTGAAATATAGCTGGATGGATATAGTACAT AAACrAAATTGGCAAGAAGGGAA |
| | SEQ ID NO: 32 | TCTATTTTTAAAAAATTGAAGTAAAATCCAAATTCATGTCATAC AGTTCAATCTCAAATTATGAAAATTTGTTGTATTAGTTTTGAGTT CAATATCAAA[T]TTAAGTAAATTTGAAAAGTAAAAGGTATTTGA AAyAAAAATTGTTATTGAAATATAGCTGGATGGATATAGTACAT AAACrAAATTGGCAAGAAGGGAA |
| M0205 | SEQ ID NO: 33 | TTAAATCTAGAGTATTCAAGTTCGCAAAAGAAAAATACACC[T]A ACTTACAGAAAAGAACAGTGAAATCCGGCGAGGCGCGGCAAAG GCAGCTGGCAGACCCTGCAG |
| | SEQ ID NO: 34 | TTAAATCTAGAGTATTCAAGTTCGCAAAAGAAAAATACACC[A]A ACTTACAGAAAAGAACAGTGAAATCCGGCGAGGCGCGGCAAAG GCAGCTGGCAGACCCTGCAG |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Resistance Assay *Pseudomonas syringae* pv. *Lachrymans*

A cucumber population was phenotyped for the presence of *Pseudomonas syringae* pv. *lachrymans* resistance. Plants were sown in May and planted 5 days after sowing in a field trial in north-west Germany. For each plant number 12 plants were used in the trial. Two weeks after planting, a natural infection became visible and plants were assessed. At that moment the trial was also inoculated with a *Pseudomonas syringae* pv. *lachrymans* isolate named psl 814/98, as described in the publications of Slomnicka et al., 2015 and Olczak-Woltman et al., 2007. The inoculum, that was kept at minus 80° C., was prepared by multiplying it in KB medium. Plants were inoculated by spraying. From two weeks after planting until six weeks after planting, whole cucumber plants were visually assessed for *Pseudomonas syringae* pv. *lachrymans* symptoms once a week using the following scale:
  1: no symptoms
  2: no symptoms to some chlorotic lesions
  3: some chlorotic lesions
  4: chlorotic lesion with minor holes
  5: many chlorotic lesions, many and big holes
All assessments and replications were collected and averaged for each plant number.

Example 2: Identification of QTLs for *Pseudomonas syringae* pv. *Lachrymans* Resistance in a Cucumber Plant (*Cucumis sativus*)

In Example 1, a cucumber plant was identified with resistance to *Pseudomonas*. Using this plant as a parent, a crossing population was made for the identification of QTLs and the creation of a genetic map. In total, marker data were derived from 268 individual cucumber plants, using 98 markers. A QTL analysis performed on these crossing populations revealed one major QTL and four minor QTLs that are linked to *Pseudomonas syringae* pv. *lachrymans* resistance. The major QTL is found on chromosome 6, and the minor QTLs are found on chromosome 2, chromosome 5, and two on chromosome 7. Sequencing of markers linked to the QTLs revealed the presence of SNPs in the marker sequences. The marker sequences of the QTLs are linked to the trait in the crossing population. The nucleotide sequence of the major QTL on chromosome 6 was identified by means of BLAST. The best BLAST hits for the sequence all resembled the sequence of the Gibberelline-20-oxidase gene.

Example 3 Validation of Individual QTLs and Combination of QTLs

To validate the effect that the Gibberelline-20-oxidase gene and optionally the other QTLs have on the resistance against *Pseudomonas syringae* pv. *lachrymans* in cucumber plants as described in Example 1 and Example 2, crossings were made between cucumber plant lines comprising a mutant allele of the Gibberelline-20-oxidase gene and optionally one or more mutant alleles of a QTL selected from the group of QTL2, QTL3, QTL4, QTLS and a cucumber plant line not containing the mutant allele of the Gibberelline-20-oxidase gene and/or mutant alleles of one or more of the QTLs. Plants from the F6 population that originated from this cross were tested for the presence of the mutant allele of the Gibberelline-20-oxidase gene and/or the presence of one or more mutant alleles of a QTL selected from the group consisting of QTL2, QTL3, QTL4, QTLS with markers sequences SEQ ID NO:1 and 2 for the mutant allele of the Gibberelline-20-oxidase gene, SEQ ID NO:7 and 8 for the mutant allele of QTL2, SEQ ID NO:13 and 14 for the mutant allele of QTL3, SEQ ID NO:25 and 26 for the mutant allele of QTL4, and SEQ ID NO:31 and 32 for the mutant allele of QTLS, as shown in Table 1 and Table 2. The average disease score of a cucumber plant having none of the mutant alleles is 5.0. A cucumber plant comprising the mutant allele of the Gibberelline-20-oxidase gene shows an average disease resistance score of 3.0. If one of the mentioned mutant alleles of a QTLs of the invention is present in addition to the presence of the mutant allele of the Gibberelline-20-oxidase gene, the average disease resistance score is 2.5. If two mutant alleles of the QTLs of the invention are present in addition to the presence of the mutant allele of the Gibberelline-20-oxidase gene, the average disease resistance score is 2.0. If three mutant alleles of the other QTLs of the invention are present, the average disease score is 1.5. A plant comprising the mutant allele of the Gibberelline-20-oxidase gene and all of the mutant alleles of the QTLs of the invention (QTL2, QTL3, QTL4 and QTLS) scores on average 1.0 on a scale of 1.0 to 5.0 as defined in Example 1.

The invention is further described by the following numbered paragraphs:

1. A cucumber plant that comprises a mutant allele of the Gibberellin-20-oxidase gene, that confers resistance to *Pseudomonas syringae* pv. *lachrymans* to the plant.

2. The cucumber plant of paragraph 1, wherein the mutant allele of the Gibberellin-20-oxidase gene comprises a SNP on a position that leads to a change in the wild type amino acid sequence of the Gibberellin-20-oxidase protein.

3. The cucumber plant of paragraph 2, wherein the SNP in the Gibberelline-20-oxidase gene is located on position 860 of the wild type nucleotide sequence SEQ ID NO:1, leading to a change in the wild type amino acid sequence of the Gibberellin-20-oxidase protein.

4. The cucumber plant of paragraph 2 or 3, wherein the change in the wild type amino acid sequence of the Gibberellin-20-oxidase protein is an amino acid substitution located on position 287 of the wild type amino acid sequence SEQ ID NO:3.

5. The cucumber plant of any of the paragraphs 2-4, wherein the SNP comprises a change from guanine to adenine.

6. The cucumber plant of any of the paragraphs 1-5 wherein the mutant allele of the Gibberellin-20-oxidase gene comprises SEQ ID NO:2.

7. The cucumber plant of any of the paragraphs 1-6, wherein the cucumber plant additionally comprises one or more mutant alleles of a QTL selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

8. A cucumber seed comprising a mutant allele of the Gibberellin-20-oxidase gene, as defined in any of the paragraphs 1-3, 5 or 6, wherein the cucumber plant grown from the seed shows resistance to *Pseudomonas syringae* pv. *lachrymans*.

9. The cucumber seed of paragraph 8, additionally comprising one or more mutant alleles of a QTL, as defined in paragraph 7, wherein the cucumber plant grown from the seed shows resistance to *Pseudomonas syringae* pv. *lachrymans*.

10. Progeny of a cucumber plant of any one of the paragraphs 1-7, or of cucumber seed of paragraph 8 or 9, comprising a mutant allele of the Gibberelline-20-oxidase gene as defined in any of the paragraphs 1-3, 5 or 6, and optionally comprising one or more mutant alleles of a QTL as defined in paragraph 7, and wherein the progeny plant shows resistance to *Pseudomonas syringae* pv. *lachrymans*.

11. Propagation material capable of developing into and/or being derived from a cucumber plant of any one of the paragraphs 1-7, wherein the propagation material is suitable for sexual reproduction, for vegetative reproduction, or suitable for tissue cultures of regenerable cells, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof, wherein the plant developing into and/or produced from the propagation material comprises a mutant allele of the Gibberelline-20-oxidase gene as defined in any of the paragraphs 1-3, 5 or 6, and optionally one or more mutant alleles of a QTL as defined in paragraph 7 and shows resistance to *Pseudomonas syringae* pv. *lachrymans*.

12. A mutant allele of the Gibberellin-20-oxidase gene, comprising a SNP on position 860 of the wild type nucleotide sequence of SEQ ID NO:1.

13. The mutant allele of the Gibberellin-20-oxidase gene of paragraph 12, wherein the SNP comprises a change from guanine to adenine.

14. The mutant allele of the Gibberellin-20-oxidase gene of paragraph 12 or 13, wherein the nucleic acid sequence of the mutant allele of the Gibberellin-20-oxidase gene comprises SEQ ID NO:2.

15. A mutant Gibberellin-20-oxidase protein, comprising a substitution on position 287 of the wild type amino acid sequence of SEQ ID NO:3.

16. The mutant Gibberellin-20-oxidase protein of paragraph 15, wherein the amino acid sequence of the mutant Gibberellin-20-oxidase protein comprises SEQ ID NO:4.

17. A marker for identification of a mutant allele of the Gibberellin-20-oxidase gene as defined in paragraph 12.

18. A marker for identification of a mutant allele of QTL2 as defined in paragraph 7, which marker is selected from the group consisting of SEQ ID No. 7 and SEQ ID No. 8.

19. A marker for identification of a mutant allele of QTL3 as defined in paragraph 7, which marker is selected from the group consisting of SEQ ID No. 13 and SEQ ID No. 14.

20. A marker for identification of a mutant allele of QTL4 as defined in paragraph 7, which marker is selected from the group of consisting of SEQ ID NO:25 and SEQ ID No. 26.

21. A marker for identification of a mutant allele of QTL5 as defined in paragraph 7, which marker is selected from the group consisting of SEQ ID No. 31 and SEQ ID No. 32.

22. Use of the mutant allele of the Gibberellin-20-oxidase gene of any of the paragraphs 12-14, or any of the markers of any of the paragraphs 17-21, or a part thereof, for identifying and/or developing a cucumber plant showing resistance to *Pseudomonas syringae* pv. *lachrymans*.

23. A method for identifying a cucumber plant showing resistance to *Pseudomonas syringae* pv. *lachrymans* comprising:

a) detecting in a cucumber plant a SNP in the wild type nucleotide sequence of SEQ ID NO:1, thereby identifying a cucumber plant showing resistance to *Pseudomonas syringae* pv. *lachrymans*;

b) optionally performing a phenotypical assay for *Pseudomonas syringae* pv. *lachrymans* resistance, to confirm that the cucumber plant is resistant to *Pseudomonas syringae* pv. *lachrymans*.

24. The method of paragraph 23, wherein the SNP in the wild type nucleotide sequence of SEQ ID NO:1 is a change from guanine to adenine on position 860.

25. The method of paragraph 23 or 24, further comprising detecting one or more mutant alleles of a QTL as defined in paragraph 7.

26. The method of any of the paragraphs 23-25, further comprising (c) selecting a cucumber plant that comprises the mutant allele of the Gibberellin-20-oxidase gene as defined in any of the paragraphs 1-3, 5 or 6 and optionally one or more mutant alleles of a QTL as defined in paragraph 7.

27. A method for producing a hybrid cucumber seed, wherein a plant grown from such seed shows resistance to *Pseudomonas syringae* pv. *lachrymans*, wherein the method comprises crossing a first parent plant with a second parent plant and harvesting the resultant seed, wherein the first parent plant and/or the second parent plant comprises a mutant allele of the Gibberellin-20-oxidase gene, wherein the mutant allele of the Gibberellin-20-oxidase gene confers resistance to *Pseudomonas syringae* pv. *lachrymans* in a plant grown from the seed.

28. The method of paragraph 27, wherein the mutant allele of the Gibberellin-20-oxidase gene comprises a SNP on position 860 of the cucumber wild type nucleotide sequence of SEQ ID NO:1, which SNP is in particular a change from guanine (G) to adenine (A).

29. The method of paragraph 27 or paragraph 28, wherein the first parent plant and/or the second parent plant additionally comprises one or more mutant alleles of a QTL as defined in paragraph 7.

30. A method for producing a cucumber plant which shows resistance to *Pseudomonas syringae* pv. *lachrymans*, wherein the method comprises:

a) crossing a plant of any one of the paragraphs 1-7 with another plant to obtain an F1 population;

b) optionally performing one or more rounds of selfing and/or crossing a plant from the F1 to obtain a further generation population;

c) selecting from the population a plant that comprises a mutant allele of the Gibberellin-20-oxidase gene and/or selecting from the population a plant showing resistance to *Pseudomonas syringae* pv. *lachrymans* by means of a phenotypical assay.

31. The method of paragraph 30, wherein the method in step (c) also comprises selecting from the population a plant that additionally comprises one or more mutant alleles of a QTL as defined in paragraph 7.

32. The method of paragraph 30 or 31, wherein the mutant allele of the Gibberellin-20-oxidase gene comprises a SNP on position 860 of the cucumber wild type nucleotide sequence of SEQ ID NO:1, which SNP is in particular a change from guanine (G) to adenine (A).

33. The method of any one of the paragraphs 30-32, wherein the cucumber plant is a plant of an inbred line, a hybrid, a doubled haploid, or of a segregating population.

34. A cell of a *Pseudomonas syringae* pv. *lachrymans* resistant cucumber plant, which cell comprises a mutant allele of the Gibberellin-20-oxidase gene, comprising a SNP on position 860 of the wild type nucleotide sequence of SEQ ID NO:1.

35. A cell of paragraph 34, furthermore comprising one or more mutant alleles selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

36. A tissue culture of a cucumber plant having resistance to *Pseudomonas syringae* pv. *lachrymans*, which tissue culture comprises a mutant allele of the Gibberellin-20-oxidase gene, comprising a SNP on position 860 of the wild type nucleotide sequence of SEQ ID NO:1.

37. A tissue culture of paragraph 36, furthermore comprising one or more mutant alleles selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

38. A method for producing a cucumber plant having resistance to *Pseudomonas syringae* pv. *lachrymans* comprising the steps of:

a) introducing mutations in a population of cucumber plants;

b) selecting a cucumber plant showing resistance to *Pseudomonas syringae* pv. *lachrymans*;

c) verifying if the plant selected under step b) has a mutation in the Gibberellin-20-oxidase gene, wherein the mutation is a SNP in the Gibberelline-20-oxidase gene represented by the wild type nucleotide sequence SEQ ID NO:1, and selecting a plant comprising such a mutation.

d) growing the plants obtained under step c)

39. A method for producing a cucumber plant showing resistance to *Pseudomonas syringae* pv. *lachrymans* comprising growing a plant from seed which was deposited under deposit number NCIMB 42582 or growing a plant from seed derived thereof.

40. A method of selecting a cucumber plant for showing resistance to *Pseudomonas syringae* pv. *lachrymans* comprising:

a) assaying genomic nucleic acids of a cucumber plant for the presence of a mutation in the wild type Gibberellin-20-oxidase gene nucleotide sequence of SEQ ID NO:1; and b) selecting the cucumber plant if said mutation is present.

41. The method of paragraph 40, wherein the selected cucumber plant shows resistance to *Pseudomonas syringae* pv. *lachrymans*.

42. The method of paragraph 40 or 41, wherein the mutation in the wild type Gibberellin-20-oxidase gene nucleotide sequence of SEQ ID NO:1 constitutes a SNP on position 860 of the wild type nucleotide sequence SEQ ID NO:1.

43. A method of selecting a cucumber plant for showing resistance to *Pseudomonas syringae* pv. *lachrymans* comprising:

a) assaying genomic nucleic acids of a cucumber plant for the presence of a mutation in the wild type Gibberellin-20-oxidase gene nucleotide sequence of SEQ ID NO:1 and for the presence of a genomic *Pseudomonas syringae* pv. *lachrymans* resistance marker genetically linked to a QTL as defined in paragraph 7, wherein said QTL is associated with *Pseudomonas syringae* pv. *lachrymans* resistance, wherein said QTL is within 20 cM or 10 cM or 5 cM of any one of the genomic *Pseudomonas syringae* pv. *lachrymans* resistance markers M5007, M5609, M5009, M1000, M3418, M2071, M1520, M0459, M5644, M5843, M0205 and M5618;

b) selecting the cucumber plant if said mutation and any of said genomic *Pseudomonas syringae* pv. *lachrymans* resistance marker are present.

44. The method of paragraph 43, wherein the selected cucumber plant shows resistance to *Pseudomonas syringae* pv. *Lachrymans*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A cucumber plant that comprises a mutant allele of the Gibberellin-20-oxidase gene, that confers resistance to *Pseudomonas syringae* pv. *lachrymans* to the plant, wherein the mutant allele of the Gibberellin-20-oxidase gene comprises a SNP on position 860 that leads to a change in the wild type amino acid sequence of the Gibberellin-20-oxidase protein.

2. The cucumber plant as claimed in claim 1, wherein the SNP in the Gibberelline-20-oxidase gene is located on position 860 of the wild type nucleotide sequence SEQ ID NO:1, leads to an amino acid substitution located on position 287 of the wild type amino acid sequence SEQ ID NO:3.

3. The cucumber plant as claimed in claim 2, wherein the SNP comprises a change from guanine to adenine.

4. The cucumber plant as claimed in claim 1, wherein the mutant allele of the Gibberellin-20-oxidase gene comprises SEQ ID NO:2.

5. The cucumber plant as claimed in claim 1, wherein the cucumber plant additionally comprises one or more mutant alleles of a QTL selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

6. A cucumber seed comprising a mutant allele of the Gibberellin-20-oxidase gene, as defined in claim 1, wherein the cucumber plant grown from the seed shows resistance to *Pseudomonas syringae* pv. *lachrymans*.

7. The cucumber seed as claimed in claim 6, additionally comprising one or more mutant alleles of a QTL, as defined in claim 5, wherein the cucumber plant grown from the seed shows resistance to *Pseudomonas syringae* pv. *lachrymans*.

8. Progeny of a cucumber plant as claimed in claim 1, or of cucumber seed as claimed in claim 6, comprising a mutant allele of the Gibberelline-20-oxidase gene as defined in claim 1, and optionally comprising one or more mutant alleles of a QTL as defined in claim 5, and wherein the progeny plant shows resistance to *Pseudomonas syringae* pv. *lachrymans*.

9. Propagation material capable of developing into and/or being derived from a cucumber plant as claimed in claim 1, wherein the propagation material is suitable for sexual reproduction, for vegetative reproduction, or suitable for tissue cultures of regenerable cells, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof, wherein the plant developing into and/or produced from the propagation material comprises a mutant allele of the Gibberelline-20-oxidase gene as defined in claim 1, and optionally one or more mutant alleles of a QTL as defined in claim 5 and shows resistance to *Pseudomonas syringae* pv. *lachrymans*.

10. A mutant allele of the Gibberellin-20-oxidase gene, comprising a SNP on position 860 of the wild type nucleotide sequence of SEQ ID NO:1.

11. The mutant allele of the Gibberellin-20-oxidase gene as claimed in claim 10, wherein the SNP comprises a change from guanine to adenine.

12. The mutant allele of the Gibberellin-20-oxidase gene as claimed in claim 10, wherein the nucleic acid sequence of the mutant allele of the Gibberellin-20-oxidase gene comprises SEQ ID NO:2.

13. A mutant Gibberellin-20-oxidase protein, comprising a substitution on position 287 of the wild type amino acid sequence of SEQ ID NO:3.

14. The mutant Gibberellin-20-oxidase protein as claimed in claim 13, wherein the amino acid sequence of the mutant Gibberellin-20-oxidase protein comprises SEQ ID NO:4.

15. A cell of a *Pseudomonas syringae* pv. *lachrymans* resistant cucumber plant, which cell comprises a mutant allele of the Gibberellin-20-oxidase gene, comprising a SNP on position 860 of the wild type nucleotide sequence of SEQ ID NO:1.

16. A cell as claimed in claim 15, furthermore comprising one or more mutant alleles selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

17. A tissue culture of a cucumber plant having resistance to *Pseudomonas syringae* pv. *lachrymans*, which tissue culture comprises a mutant allele of the Gibberellin-20-oxidase gene, comprising a SNP on position 860 of the wild type nucleotide sequence of SEQ ID NO:1.

18. A tissue culture as claimed in claim 17, furthermore comprising one or more mutant alleles selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to *Pseudomonas syringae* pv. *lachrymans*; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

* * * * *

UNITED STATES PATENT AND TRADEMARK OFFICE
CERTIFICATE OF CORRECTION

PATENT NO. : 11,317,574 B2
APPLICATION NO. : 16/594755
DATED : May 3, 2022
INVENTOR(S) : Cornelis Van Der Maas It is certified that error appears in the above-identified patent and that said Letters Patent is hereby corrected as shown below:

In the Claims

Column 47, Lines 65-67-Column 48, Lines 57-58, Claim 2 should read:
2. The cucumber plant as claimed in claim 1, wherein the SNP in the Gibberelline-20-oxidase gene located on position 860 of the wild type nucleotide sequence SEQ ID NO:1, leads to an amino acid substitution located on position 287 of the wild type amino acid sequence SEQ ID NO:3.

Column 48, Lines 59-60, Claim 3 should read:
3. The cucumber plant as claimed in claim 1, wherein the SNP comprises a change from guanine to adenine.

Column 48, Line 64, Claim 5 should read as:
5. The cucumber plant as claimed in claim 1, wherein the cucumber plant additionally comprises one or more mutant alleles of a QTL selected from the group consisting of QTL2, QTL3, QTL4, and QTL5; wherein QTL2 is located on chromosome 2; QTL3 is located on chromosome 5, QTL4 is located on chromosome 7, and QTL5 is located on chromosome 7, which mutant alleles confer resistance to Pseudomonas syringae pv. lachrymans; and wherein the mutant alleles of said QTLs are as found in a cucumber plant, representative seed of which was deposited under deposit number NCIMB 42582; wherein in the seeds of the deposit, QTL2 is located between molecular markers M5007, represented by SEQ ID NO:5 and SEQ ID NO:6, and M5609, represented by SEQ ID NO:9 and SEQ ID NO:10, and is linked to sequence SEQ ID NO:8 of marker M5009; wherein in the seeds of the deposit QTL3 is located between molecular markers M1000, represented by SEQ ID NO:11 and SEQ ID NO:12, and M3418, represented by SEQ ID NO:15 and SEQ ID NO:16, and is linked to sequence SEQ ID NO:14 of marker M2071; wherein in the seeds of the deposit QTL4 is located between molecular markers M1520, represented by SEQ ID NO:23 and SEQ ID NO:24, and M0459 represented by SEQ ID NO:27 and SEQ ID NO:28, and is linked to sequence SEQ ID NO:26 of marker M5644; wherein in the seeds of the deposit QTL5 is located between molecular markers M5843, represented by SEQ ID NO:29 and SEQ ID NO:30, and M0205, represented by SEQ ID NO:33 and SEQ ID NO:34, and is linked to sequence SEQ ID NO:32 of marker M5618.

Signed and Sealed this
Sixteenth Day of August, 2022

Katherine Kelly Vidal
*Director of the United States Patent and Trademark Office*

```
                           SEQUENCE LISTING

<160> NUMBER OF SEQ ID NOS: 34

<210> SEQ ID NO 1
<211> LENGTH: 1113
<212> TYPE: DNA
<213> ORGANISM: Cucumis sativus
<220> FEATURE:
<223> OTHER INFORMATION: Gibberellin-20-oxidase (GAOX2) gene

<400> SEQUENCE: 1
atggaatcga cgacgacggt ggggagggtg gccggaataa tattgccgac gatggtagac      60
aagaagaaga aactaccaag ggaattcgtg tggccacgag gggagttggc aggggaggaa     120 agagggagt tgaaagagcc gttgatagac ttaggggat tcaggagagg ggaggaagag      180
gcgacggcgg aggcggcggc gatggtgagg atggcatgta tgaaacatgg ggtgtttcag     240
gtgacgaatc acggagtgga agaggagctg ataaaggcgg cgtatgaaga aggggagggg     300
atatttaaga tgccattagt gaagaaaata agcgtgggga aaaaccggg gagagtgtcg      360 ggatattcag gagctcatgc agatagattc tcttcaaaac ttccatggaa agagaccttc     420
tcttttgagt attctaatga tgattctcaa cctctacatg ttcttcatca ctttaaatca     480
ttgttcggtt gcgacttcga gaatactgga tgggtatacc aaagatactg tgaagaaatg     540
acaagaacag cattaatgat aatggagctt ctagcaataa gtttgggagt agagagatat     600
cattacagga agttctttga agatggaaag tcaataatga gatgcaatta ctatccacca     660
tgtgagaatg caagcctgac tttaggcaca ggccctcatt gtgacccaac ttcactcact     720
attctccatc aagatcaagt tggtggcctt gaagttttg ctaacaacgc ttggctctct      780
gtcaaaccta gacctgatgc tttggttatt aacattggtg acactttat ggcactgtcg      840 aatggagcgt acaagagctg tctgcatagg gcagtggtga caggaagag agagagaagg     900 tcattggtgt tctttgtgtg cccaaaagat gataaagtgg tgagacccc acaagatttg      960 gtgggcagag aagggccaag acagtaccct gatttcacat ggtcagagct tttggagttt    1020
acacaaaaac attacagagc tgatgttgct acactccaaa gctttgtcca ctggcttcaa    1080
gctaaacctc accctccaaa aattccattt taa                                 1113

<210> SEQ ID NO 2
<211> LENGTH: 1113
<212> TYPE: DNA
<213> ORGANISM: Cucumis sativus
<220> FEATURE:
<223> OTHER INFORMATION: Gibberellin-20-oxidase (GAOX2) gene

<400> SEQUENCE: 2
atggaatcga cgacgacggt ggggagggtg gccggaataa tattgccgac gatggtagac      60
aagaagaaga aactaccaag ggaattcgtg tggccacgag gggagttggc aggggaggaa     120 agagggagt tgaaagagcc gttgatagac ttaggggat tcaggagagg ggaggaagag      180
gcgacggcgg aggcggcggc gatggtgagg atggcatgta tgaaacatgg ggtgtttcag     240
gtgacgaatc acggagtgga agaggagctg ataaaggcgg cgtatgaaga aggggagggg     300
atatttaaga tgccattagt gaagaaaata agcgtgggga aaaaccggg gagagtgtcg      360
```

```
ggatattcag gagctcatgc agatagattc tcttcaaaac ttccatggaa agagaccttc    420
tcttttgagt attctaatga tgattctcaa cctctacatg ttcttcatca ctttaaatca    480
ttgttcggtt gcgacttcga gaatactgga tgggtatacc aaagatactg tgaagaaatg    540
acaagaacag cattaatgat aatggagctt ctagcaataa gtttgggagt agagagatat    600
cattacagga agttctttga agatggaaag tcaataatga gatgcaatta ctatccacca    660
tgtgagaatg caagcctgac tttaggcaca ggccctcatt gtgacccaac ttcactcact    720
attctccatc aagatcaagt tggtggcctt gaagttttg ctaacaacgc ttggctctct     780
gtcaaaccta gacctgatgc tttggttatt aacattggtg acacttttat ggcactgtcg    840
aatggagcgt acaagagcta tctgcatagg gcagtggtga acaggaagag agagagaagg    900
tcattggtgt tctttgtgtg cccaaaagat gataaagtgg tgagaccccc acaagatttg    960
gtgggcagag aagggccaag acagtaccct gatttcacat ggtcagagct tttggagttt   1020
acacaaaaac attacagagc tgatgttgct acactccaaa gctttgtcca ctggcttcaa   1080
gctaaacctc accctccaaa aattccattt taa                                1113
```

<210> SEQ ID NO 3
<211> LENGTH: 370
<212> TYPE: PRT
<213> ORGANISM: Cucumis sativus
<220> FEATURE:
<223> OTHER INFORMATION: Gibberelline-20-oxidase amino acid sequence

<400> SEQUENCE: 3

```
Met Glu Ser Thr Thr Thr Val Gly Arg Val Ala Gly Ile Ile Leu Pro
1               5                   10                  15

Thr Met Val Asp Lys Lys Lys Leu Pro Arg Glu Phe Val Trp Pro
        20                  25                  30

Arg Gly Glu Leu Ala Gly Glu Arg Gly Glu Leu Lys Glu Pro Leu
        35                  40                  45

Ile Asp Leu Gly Gly Phe Arg Arg Gly Glu Glu Ala Thr Ala Glu
    50                  55                  60

Ala Ala Ala Met Val Arg Met Ala Cys Met Lys His Gly Val Phe Gln
65                  70                  75                  80

Val Thr Asn His Gly Val Glu Glu Leu Ile Lys Ala Ala Tyr Glu
            85                  90                  95

Glu Gly Glu Gly Ile Phe Lys Met Pro Leu Val Lys Lys Ile Ser Val
                100                 105                 110

Gly Lys Lys Pro Gly Arg Val Ser Gly Tyr Ser Gly Ala His Ala Asp
            115                 120                 125

Arg Phe Ser Ser Lys Leu Pro Trp Lys Glu Thr Phe Ser Phe Glu Tyr
        130                 135                 140

Ser Asn Asp Asp Ser Gln Pro Leu His Val Leu His Phe Lys Ser
145                 150                 155                 160

Leu Phe Gly Cys Asp Phe Glu Asn Thr Gly Trp Val Tyr Gln Arg Tyr
                165                 170                 175

Cys Glu Glu Met Thr Arg Thr Ala Leu Met Ile Met Glu Leu Leu Ala
            180                 185                 190

Ile Ser Leu Gly Val Glu Arg Tyr His Tyr Arg Lys Phe Phe Glu Asp
        195                 200                 205

Gly Lys Ser Ile Met Arg Cys Asn Tyr Tyr Pro Pro Cys Glu Asn Ala
    210                 215                 220
```

```
Ser Leu Thr Leu Gly Thr Gly Pro His Cys Asp Pro Thr Ser Leu Thr
225                 230                 235                 240

Ile Leu His Gln Asp Gln Val Gly Gly Leu Glu Val Phe Ala Asn Asn
                245                 250                 255

Ala Trp Leu Ser Val Lys Pro Arg Pro Asp Ala Leu Val Ile Asn Ile
            260                 265                 270

Gly Asp Thr Phe Met Ala Leu Ser Asn Gly Ala Tyr Lys Ser Cys Leu
        275                 280                 285

His Arg Ala Val Val Asn Arg Lys Arg Glu Arg Ser Leu Val Phe
    290                 295                 300

Phe Val Cys Pro Lys Asp Asp Lys Val Val Arg Pro Gln Asp Leu
305             310                 315                 320

Val Gly Arg Glu Gly Pro Arg Gln Tyr Pro Asp Phe Thr Trp Ser Glu
                325                 330                 335

Leu Leu Glu Phe Thr Gln Lys His Tyr Arg Ala Asp Val Ala Thr Leu
            340                 345                 350

Gln Ser Phe Val His Trp Leu Gln Ala Lys Pro His Pro Pro Lys Ile
        355                 360                 365

Pro Phe
    370

<210> SEQ ID NO 4
<211> LENGTH: 370
<212> TYPE: PRT
<213> ORGANISM: Cucumis sativus
<220> FEATURE:
<223> OTHER INFORMATION: Gibberelline-20-oxidase amino acid sequence

<400> SEQUENCE: 4

Met Glu Ser Thr Thr Thr Val Gly Arg Val Ala Gly Ile Ile Leu Pro
1               5                   10                  15

Thr Met Val Asp Lys Lys Lys Leu Pro Arg Glu Phe Val Trp Pro
                20                  25                  30

Arg Gly Glu Leu Ala Gly Glu Arg Gly Glu Leu Lys Glu Pro Leu
            35                  40                  45

Ile Asp Leu Gly Gly Phe Arg Arg Gly Glu Glu Ala Thr Ala Glu
    50                  55                  60

Ala Ala Ala Met Val Arg Met Ala Cys Met Lys His Gly Val Phe Gln
65                  70                  75                  80

Val Thr Asn His Gly Val Glu Glu Leu Ile Lys Ala Ala Tyr Glu
                85                  90                  95

Glu Gly Glu Gly Ile Phe Lys Met Pro Leu Val Lys Lys Ile Ser Val
                100                 105                 110

Gly Lys Lys Pro Gly Arg Val Ser Gly Tyr Ser Gly Ala His Ala Asp
            115                 120                 125

Arg Phe Ser Ser Lys Leu Pro Trp Lys Glu Thr Phe Ser Phe Glu Tyr
    130                 135                 140

Ser Asn Asp Asp Ser Gln Pro Leu His Val Leu His His Phe Lys Ser
145                 150                 155                 160

Leu Phe Gly Cys Asp Phe Glu Asn Thr Gly Trp Val Tyr Gln Arg Tyr
                165                 170                 175

Cys Glu Glu Met Thr Arg Thr Ala Leu Met Ile Met Glu Leu Leu Ala
            180                 185                 190

Ile Ser Leu Gly Val Glu Arg Tyr His Tyr Arg Lys Phe Phe Glu Asp
        195                 200                 205
```

```
Gly Lys Ser Ile Met Arg Cys Asn Tyr Tyr Pro Pro Cys Glu Asn Ala
            210                 215                 220

Ser Leu Thr Leu Gly Thr Gly Pro His Cys Asp Pro Thr Ser Leu Thr
225                 230                 235                 240

Ile Leu His Gln Asp Gln Val Gly Gly Leu Glu Val Phe Ala Asn Asn
                245                 250                 255

Ala Trp Leu Ser Val Lys Pro Arg Pro Asp Ala Leu Val Ile Asn Ile
                260                 265                 270

Gly Asp Thr Phe Met Ala Leu Ser Asn Gly Ala Tyr Lys Ser Tyr Leu
            275                 280                 285

His Arg Ala Val Val Asn Arg Lys Arg Glu Arg Ser Leu Val Phe
290                 295                 300

Phe Val Cys Pro Lys Asp Asp Lys Val Val Arg Pro Gln Asp Leu
305                 310                 315                 320

Val Gly Arg Glu Gly Pro Arg Gln Tyr Pro Asp Phe Thr Trp Ser Glu
                325                 330                 335

Leu Leu Glu Phe Thr Gln Lys His Tyr Arg Ala Asp Val Ala Thr Leu
            340                 345                 350

Gln Ser Phe Val His Trp Leu Gln Ala Lys Pro His Pro Pro Lys Ile
            355                 360                 365

Pro Phe
    370

<210> SEQ ID NO 5
<211> LENGTH: 201
<212> TYPE: DNA
<213> ORGANISM: Cucumis sativus
<220> FEATURE:
<223> OTHER INFORMATION: M5007

<400> SEQUENCE: 5
ttgaaaaatt aaatcttcts tatgatatta tccgctgtaa atctatcctt aataagcatt      60
agaactgtat ttgttctttt ataaaaaaaa aatctaactc tttccaattt atttaaaaaa     120
agtacattct ctatctacta tcattttgtt tgtctatcac ccaccctcc ctaccttcat      180 cctcagatag catcttctyg c                                                201

<210> SEQ ID NO 6
<211> LENGTH: 201
<212> TYPE: DNA
<213> ORGANISM: Cucumis sativus
<220> FEATURE:
<223> OTHER INFORMATION: M5007

<400> SEQUENCE: 6
ttgaaaaatt aaatcttcts tatgatatta tccgctgtaa atctatcctt aataagcatt      60
agaactgtat ttgttctttt ataaaaaaaa aatctaactc attccaattt atttaaaaaa     120
agtacattct ctatctacta tcattttgtt tgtctatcac ccaccctcc ctaccttcat      180 cctcagatag catcttctyg c                                                201

<210> SEQ ID NO 7
<211> LENGTH: 201
<212> TYPE: DNA
<213> ORGANISM: Cucumis sativus
<220> FEATURE:
<223> OTHER INFORMATION: M5009

<400> SEQUENCE: 7
```

```
tttatttcat aatttctatc tatttagttc acaaattttta ataaattctt tcaattttat    60
ctaacttatt catgcattaa aataaacatt taacgttgaa tcaatataga atayaacaat    120
ttgttataga aagctttcaa tatgtcagta ttagctttta attaatcgat tagacttgta   180
attagaaaaa taaaaaatct t                                             201

<210> SEQ ID NO 8
<211> LENGTH: 201
<212> TYPE: DNA
<213> ORGANISM: Cucumis sativus
<220> FEATURE:
<223> OTHER INFORMATION: M5009

<400> SEQUENCE: 8
tttatttcat aatttctatc tatttagttc acaaattttta ataaattctt tcaattttat    60
ctaacttatt catgcattaa aataaacatt taacgttgaa ccaatataga atayaacaat    120
ttgttataga aagctttcaa tatgtcagta ttagctttta attaatcgat tagacttgta   180
attagaaaaa taaaaaatct t                                             201

<210> SEQ ID NO 9
<211> LENGTH: 201
<212> TYPE: DNA
<213> ORGANISM: Cucumis sativus
<220> FEATURE:
<223> OTHER INFORMATION: M5609

<400> SEQUENCE: 9
ttctattttt aatattattt atttatcgat ataggtcatg aatgcgacca aaatctcaca    60
cttgagacta catctcacta aaagaccgta gataaaataa agtatatgtg tagtatttct   120
cattggtaga gacgtttttg acaaaaccaa aggcaaaagt ctactacatc aatttgacaa   180
tttctatcta aaaggaataa t                                             201

<210> SEQ ID NO 10
<211> LENGTH: 201
<212> TYPE: DNA
<213> ORGANISM: Cucumis sativus
<220> FEATURE:
<223> OTHER INFORMATION: M5609

<400> SEQUENCE: 10
ttctattttt aatattattt atttatcgat ataggtcatg aatgcgacca aaatctcaca    60
cttgagacta catctcacta aaagaccgta gataaaataa ggtatatgtg tagtatttct   120
cattggtaga gacgtttttg acaaaaccaa aggcaaaagt ctactacatc aatttgacaa   180
tttctatcta aaaggaataa t                                             201

<210> SEQ ID NO 11
<211> LENGTH: 251
<212> TYPE: DNA
<213> ORGANISM: Cucumis sativus
<220> FEATURE:
<223> OTHER INFORMATION: M1000

<400> SEQUENCE: 11
ttaaccaaac cagattctgt ctctcgtgac atagaattag atcttcacct cattcaaaat    60
ggtctgcatc ggacatcacg tttcgagatt gcaatgcaag tggttcggaa catggttgct   120
actgttggtg actcgaatgt ctggttagct ggccattccc ttggatccgc catggcaatg   180
cttgctggaa gaaccatggc aagaacaggc attttcctca aatcataccct cttcaatcct   240
```
ccattcttgg c                                                           251

<210> SEQ ID NO 12
<211> LENGTH: 251
<212> TYPE: DNA
<213> ORGANISM: Cucumis sativus
<220> FEATURE:
<223> OTHER INFORMATION: M1000

<400> SEQUENCE: 12
ttaaccaaac cagattctgt ctctcgtgac atagaattag atcttcacct cattcaaaat      60
ggtctgcatc ggacatcacg tttcgagatt gcaatgcaag tggttcggaa catggttgct    120
actgttggtg actcgaatgt ctggttagct ggccattccc ttggatccgc catggcaatg    180
cttgctggaa gaaccatggc aagaacgggc attttcctca aatcatacct cttcaatcct    240
ccattcttgg c                                                           251

<210> SEQ ID NO 13
<211> LENGTH: 201
<212> TYPE: DNA
<213> ORGANISM: Cucumis sativus
<220> FEATURE:
<223> OTHER INFORMATION: M2071

<400> SEQUENCE: 13
aaccaccatt tgtccccatc tagagctatt tactccgata gattcatacc cagtagatct      60
ggttctaatt ttgccctttt tgatatctcc cctgtttcca cttccactc tgatggtcgt    120
gaggatactt ctactgctta cgctacccct cttcgtactg ctttgtttgg tcctgattct    180
ggtgtaatcc ctcctgctac t                                                201

<210> SEQ ID NO 14
<211> LENGTH: 201
<212> TYPE: DNA
<213> ORGANISM: Cucumis sativus
<220> FEATURE:
<223> OTHER INFORMATION: M2071

<400> SEQUENCE: 14
aaccaccatt tgtccccatc tagagctatt tactccgata gattcatacc cagtagatct      60
ggttctaatt ttgccctttt tgatatctcc cctgtttcca attccactc tgatggtcgt    120
gaggatactt ctactgctta cgctacccct cttcgtactg ctttgtttgg tcctgattct    180
ggtgtaatcc ctcctgctac t                                                201

<210> SEQ ID NO 15
<211> LENGTH: 200
<212> TYPE: DNA
<213> ORGANISM: Cucumis sativus
<220> FEATURE:
<223> OTHER INFORMATION: M3418

<400> SEQUENCE: 15
caacaaaaaa gtggacttca tttctaagct aggcatcgaa tataaaacaa gcactaaaca      60
aattgataga atcactagat aatcaagcta actaaaatac gggagaatac gtaccttaat    120
atgagcctat cccagtcata aaaccctgca tttatcaaat tccgtgttgt acattccctc    180
tgcttttcgc ttcttccagt                                                  200

<210> SEQ ID NO 16

```
<211> LENGTH: 200
<212> TYPE: DNA
<213> ORGANISM: Cucumis sativus
<220> FEATURE:
<223> OTHER INFORMATION: M3418

<400> SEQUENCE: 16
caacaaaaaa gtggacttca tttctaagct aggcatcgaa tataaaacaa gcactaaaca      60
aattgataga atcactagat aatcaagcta actaaaatac ggggaatac gtaccttaat     120 atgagcctat cccagtcata aaccctgca tttatcaaat tccgtgttgt acattccctc     180
tgcttttcgc ttcttccagt                                                 200

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 679
<212> TYPE: DNA
<213> ORGANISM: Cucumis sativus
<220> FEATURE:
<223> OTHER INFORMATION: M1520

<400> SEQUENCE: 23
atcagtaagg taaagatttg gttaaagtgt ttatttaacg catttgcaat ccatttgagt      60
tgacatggtc tgatgcaaaa catcttgtgc tcgagcatat aaaaaagaga ggtaaatctc     120
acctgcgaca tcgacttgtt tgctcgggct agccgaaaca catttaacat acaataaaac     180
acagagtaca caatatgatt tccaaaagta tatatgctaa cttaaatatt atttgactct     240
ggtacatcac aatgttgtca aagttcatga atgcactttc cactgatgaa atctataact     300
tttgtaactg cttgatccag tgcagcagag actgtagcta gattctgcaa gaattcttcg     360
```

```
gcagttggtt tttcgccatc tacgatatcs gttacagctt ttagaaatat ggcaggaact      420
ttgaatatat cagccacata ggctactgct gctccctcca tatctttaac tgtggcatca      480
ttagctacaa tcgatgattc atcttgtgca gacatgtcta gtgaatcacc cgttgataat      540
ttgccaacct ttagatcaag ttccttatgg agattgggcg ttttccatgc ttgcttcaat      600
ccgactccat ataaatcaaa aactggaata ggtatacgtc tgtcatggaa ggcacactcg      660
ggataccgag aacacgtcg                                                   679
```

<210> SEQ ID NO 24
<211> LENGTH: 679
<212> TYPE: DNA
<213> ORGANISM: Cucumis sativus
<220> FEATURE:
<223> OTHER INFORMATION: M1520

<400> SEQUENCE: 24

```
atcagtaagg taaagatttg gttaaagtgt ttatttaacg catttgcaat ccatttgagt       60
tgacatggtc tgatgcaaaa catcttgtgc tcgagcatat aaaaagaga ggtaaatctc      120 acctgcgaca tcgacttgtt tgctcgggct agccgaaaca catttaacat acaataaaac      180
acagagtaca caatatgatt tccaaaagta tatatgctaa cttaaatatt atttgactct      240
ggtacatcac aatgttgtca aagttcatga atgcactttc cactgatgaa atctataact      300
tttgtaactg cttgatccag tgcagcagag actgtagcta gattctgcaa gaattcttca      360
gcagttggtt tttcgccatc tacgatatcs gttacagctt ttagaaatat ggcaggaact      420
ttgaatatat cagccacata ggctactgct gctccctcca tatctttaac tgtggcatca      480
ttagctacaa tcgatgattc atcttgtgca gacatgtcta gtgaatcacc cgttgataat      540
ttgccaacct ttagatcaag ttccttatgg agattgggcg ttttccatgc ttgcttcaat      600
ccgactccat ataaatcaaa aactggaata ggtatacgtc tgtcatggaa ggcacactcg      660
ggataccgag aacacgtcg                                                   679
```

<210> SEQ ID NO 25
<211> LENGTH: 201
<212> TYPE: DNA
<213> ORGANISM: Cucumis sativus
<220> FEATURE:
<223> OTHER INFORMATION: M5644

<400> SEQUENCE: 25

```
ctgtaaacct tgagaggagg taaaaaagat aagtcaattt ttcattttc aaaacaactt       60 tcgttgagaa aaatgaaag aatagagcat acaagggag atcagctaaa attaggggct      120
ccaactatac aagacaaaaa gtcaaattca ggtcacagaa atacgcaaag aagaaaacat      180
gtcctcaatg ccaaatacat c                                                201
```

<210> SEQ ID NO 26
<211> LENGTH: 201
<212> TYPE: DNA
<213> ORGANISM: Cucumis sativus
<220> FEATURE:
<223> OTHER INFORMATION: M5644

<400> SEQUENCE: 26

```
ctgtaaacct tgagaggagg taaaaaagat aagtcaattt ttcattttc aaaacaactt       60 tcgttgagaa aaatgaaag aatagagcat acaagggag ctcagctaaa attaggggct      120
```

```
ccaactatac aagacaaaaa gtcaaattca ggtcacagaa atacgcaaag aagaaaacat    180
gtcctcaatg ccaaatacat c                                              201
```

```
<210> SEQ ID NO 27
<211> LENGTH: 200
<212> TYPE: DNA
<213> ORGANISM: Cucumis sativus
<220> FEATURE:
<223> OTHER INFORMATION: M0459

<400> SEQUENCE: 27
aagcttcaac ttttttcttt ttttttttgt ttcattttcg ctcttaaatt atgcttcaca     60
aaatggaaaa tactttatga atgggaaggt aaaagaagaa caatcttgag acatgaacta   120
tgtgaaaata atttttttaa aaaaatggta tttcttttct taataaacca ttactttcca   180
ctctggatag cagtgtactt                                               200
```

```
<210> SEQ ID NO 28
<211> LENGTH: 200
<212> TYPE: DNA
<213> ORGANISM: Cucumis sativus
<220> FEATURE:
<223> OTHER INFORMATION: M0459

<400> SEQUENCE: 28
aagcttcaac ttttttcttt ttttttttgt ttcattttcg ctcttaaatt atgcttcaca     60
aaatggaaaa tactttatga atgggaaggt aaaagaagaa gaatcttgag acatgaacta   120
tgtgaaaata atttttttaa aaaaatggta tttcttttct taataaacca ttactttcca   180
ctctggatag cagtgtactt                                               200
```

```
<210> SEQ ID NO 29
<211> LENGTH: 259
<212> TYPE: DNA
<213> ORGANISM: Cucumis sativus
<220> FEATURE:
<223> OTHER INFORMATION: M5843

<400> SEQUENCE: 29
aatctatcac tttgtcacct gttttttgtga agcctgattg tattttgttg atatctgctt    60
ttcgttaggt tttttaaga tcaagtaaaa ttgtaccatt aaactgcttg catctctcat    120
ctgtaggcag cagaagattt tttggttcac ctatttgaag ataccatgct gtgtgctatt   180
catgccaaac gtgtaactat cagtaagtca atcttcacat atttgagttt tgttccaatt   240
ttgattatgg tagctattt                                                259
```

```
<210> SEQ ID NO 30
<211> LENGTH: 259
<212> TYPE: DNA
<213> ORGANISM: Cucumis sativus
<220> FEATURE:
<223> OTHER INFORMATION: M5843

<400> SEQUENCE: 30
aatctatcac tttgtcacct gttttttgtga agcctgattg tattttgttg atatctgctt    60
ttcgttaggt tttttaaga tcaagtaaaa ttgtaccatt aaactgcttg catctctcat    120
ctgtagacag cagaagattt tttggttcac ctatttgaag ataccatgct gtgtgctatt   180
catgccaaac gtgtaactat cagtaagtca atcttcacat atttgagttt tgttccaatt   240
ttgattatgg tagctattt                                                259
```

```
<210> SEQ ID NO 31
<211> LENGTH: 201
<212> TYPE: DNA
<213> ORGANISM: Cucumis sativus
<220> FEATURE:
<223> OTHER INFORMATION: M5618

<400> SEQUENCE: 31 tctattttt  aaaaaattga  agtaaaatcc  aaattcatgt  catacagttc  aatctcaaat      60
tatgaaaatt  tgttgtatta  gttttgagtt  caatatcaaa  gttaagtaaa  tttgaaaagt     120
aaaaggtatt  tgaaayaaaa  attgttattg  aaatatagct  ggatggatat  agtacataaa    180
craaattggc  aagaaaggga  a                                                 201

<210> SEQ ID NO 32
<211> LENGTH: 201
<212> TYPE: DNA
<213> ORGANISM: Cucumis sativus
<220> FEATURE:
<223> OTHER INFORMATION: M5618

<400> SEQUENCE: 32 tctattttt  aaaaaattga  agtaaaatcc  aaattcatgt  catacagttc  aatctcaaat      60
tatgaaaatt  tgttgtatta  gttttgagtt  caatatcaaa  tttaagtaaa  tttgaaaagt     120
aaaaggtatt  tgaaayaaaa  attgttattg  aaatatagct  ggatggatat  agtacataaa    180
craaattggc  aagaaaggga  a                                                 201

<210> SEQ ID NO 33
<211> LENGTH: 106
<212> TYPE: DNA
<213> ORGANISM: Cucumis sativus
<220> FEATURE:
<223> OTHER INFORMATION: M0205

<400> SEQUENCE: 33
ttaaatctag  agtattcaag  ttcgcaaaag  aaaaatacac  ctaacttaca  gaaaagaaca     60
gtgaaatccg  gcgaggcgcg  gcaaaggcag  ctggcagacc  ctgcag                    106

<210> SEQ ID NO 34
<211> LENGTH: 106
<212> TYPE: DNA
<213> ORGANISM: Cucumis sativus
<220> FEATURE:
<223> OTHER INFORMATION: M0205

<400> SEQUENCE: 34
ttaaatctag  agtattcaag  ttcgcaaaag  aaaaatacac  caaacttaca  gaaaagaaca     60
gtgaaatccg  gcgaggcgcg  gcaaaggcag  ctggcagacc  ctgcag                    106
```